Figure 1:
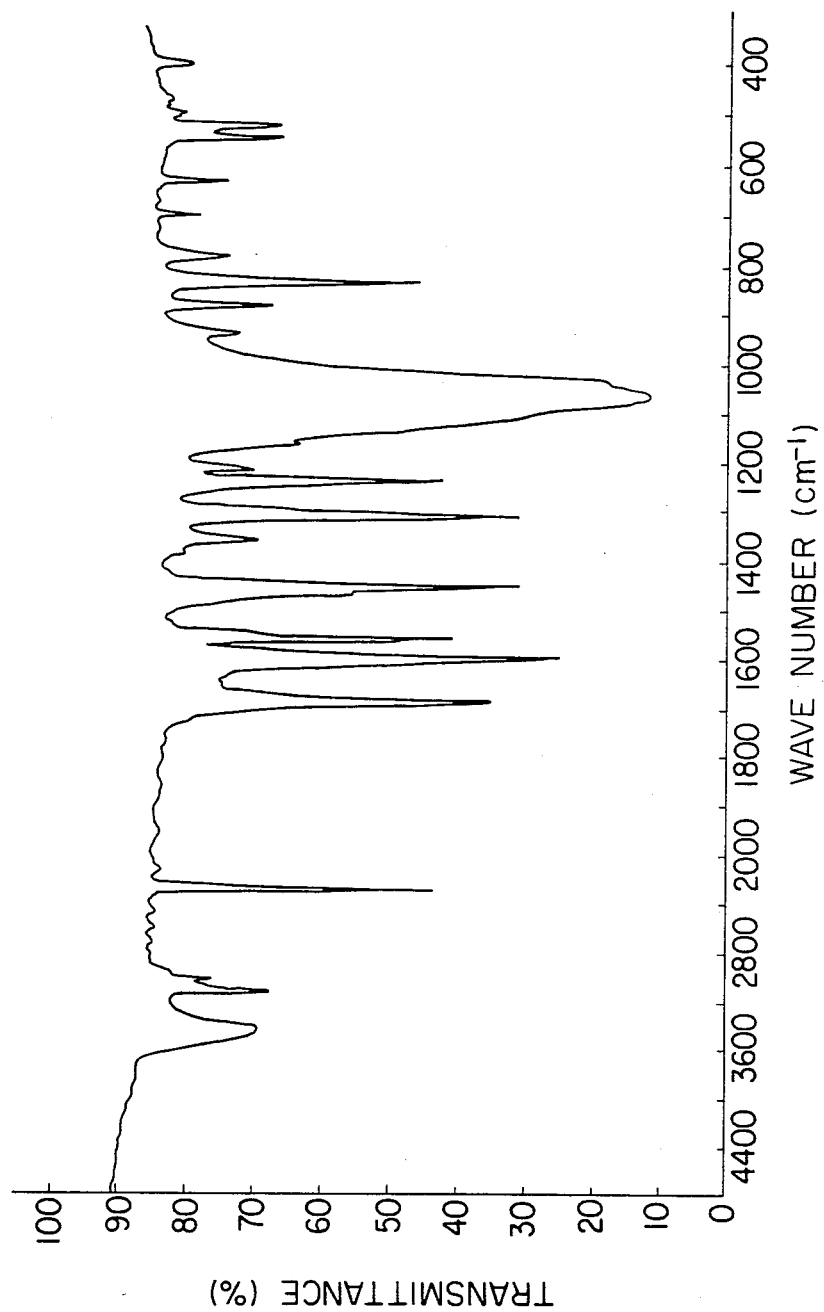

United States Patent [19]

Tsutsui

[11] Patent Number: 4,540,643
[45] Date of Patent: Sep. 10, 1985

[54] TETRAZONIUM SALT COMPOUNDS, NOVEL DISAZO COMPOUNDS, METHOD FOR THE PRODUCTION THEREOF AND DISAZO COMPOUND-CONTAINING ELECTROPHOTOGRAPHIC ELEMENTS

[75] Inventor: Kyoji Tsutsui, Mishima, Japan

[73] Assignee: Ricoh Co., Ltd., Tokyo, Japan

[21] Appl. No.: 597,991

[22] Filed: Apr. 9, 1984

[30] Foreign Application Priority Data

Apr. 26, 1983 [JP] Japan .................................. 58-73177
Apr. 28, 1983 [JP] Japan .................................. 58-75586

[51] Int. Cl.³ .................................................. G03G 5/06
[52] U.S. Cl. ......................................... 430/58; 430/72; 430/75; 534/759
[58] Field of Search ....................... 430/57, 58, 59, 72, 430/75; 534/759, 761

[56] References Cited

U.S. PATENT DOCUMENTS 3,959,250 5/1976 Heinrich et al. ................. 534/759
4,251,613 2/1981 Sasaki et al. ....................... 430/58

Primary Examiner—John D. Welsh
Attorney, Agent, or Firm—Flynn, Thiel, Boutell & Tanis

[57] ABSTRACT

The present invention provides a tetrazoneum salt compound represented by the general formula (I):

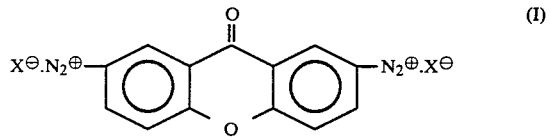

(wherein, X stands for an anion functional group.); a disazo compound represented by the general formula (II):

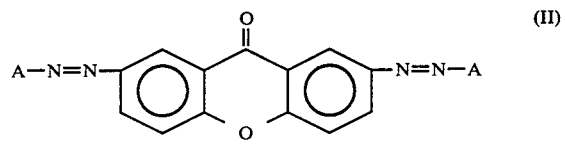

[wherein, A stands for (Abstract continued on next page.)

4,540,643
Page 2

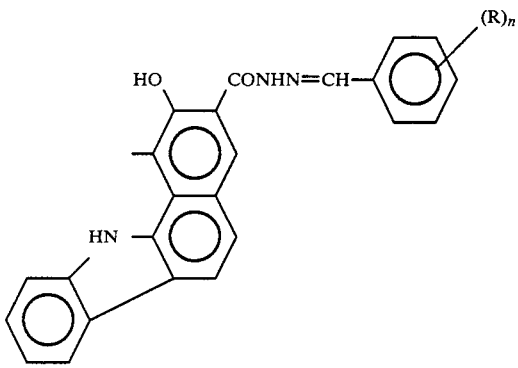

(wherein, R stands for an alkyl group, an alkoxy group, a nitro group, halogen, a cyano group or a halomethyl group, n stands for an integer of 0, 1, 2 or 3, and in case n is an integer of 2 or 3 R may be the same or different.); a method for the production thereof, and electrophotographic elements using the same or like disazo compounds as the charge carrier generating materials.

16 Claims, 7 Drawing Figures

TETRAZONIUM SALT COMPOUNDS, NOVEL DISAZO COMPOUNDS, METHOD FOR THE PRODUCTION THEREOF AND DISAZO COMPOUND-CONTAINING ELECTROPHOTOGRAPHIC ELEMENTS

BACKGROUND OF THE INVENTION (a) Field of the Invention

The present invention relates to novel tetrazonium salt compounds, novel disazo compounds and the method of producing said compounds, and electrophotographic elements containing these disazo compounds and the like, in particular relates to electrophotographic elements provided with photosensitive layers containing said disazo compounds as materials that generate charge carriers when exposed to light (which will be called charge carrier generating materials hereinafter), preferably multilayer type electrophotographic elements comprising layers containing said charge carrier generating materials (which will be called charge carrier generating layers hereinafter) and layers containing materials which receive the charge carriers generated in said charge carrier generating layers and transfer them (which will be called charge transfer materials hereinafter) respectively.

(b) Description of the Prior Art

As the conventional electrophotographic elements, there can be enumerated inorganic and organic ones. The inorganic system electrophotographic elements include those using selenium and its alloys and those prepared by dispersing dye-sensitized zinc oxide in binder resins, while as the organic system electrophotographic elements, there can be typically enumerated those using a charge transfer complex of 2,4,7-trinitro-9-fluorenone (which will be called TNF hereinafter) and poly-N-vinylcarbazole (which will be called PVK) and the like. But, it is also fact that these electrophotographic elements have various advantages, while have various disadvantages. For instance, the selenium electrophotographic elements which have presently been used universally are defective in that the manufacturing conditions are strict, the manufacturing cost is expensive, it is difficult to processing it into belt-like due to the absence of flexibility, attention must be paid in handling them because they are highly sensitive to heat and mechanical impact. Referring to zinc oxide elements, the manufacturing cost is low because they can be manufactured by applying cheap zinc oxides onto substrates, but said electrophotographic elements are defective mechanically in that they are generally inferior in sensitivity, surface-smoothness, solidity, tensile strength, friction resistance and the like and involve various problems to be solved in respect of durability and the like as the elements used repeatedly in copying plain papers. The elements electrophotographic using charge transfer complexes of TNF and PVK are so inferior in sensitivity that they are not suitable for the elements for use in high-speed copying machines.

Of late years, a wide range of studies have been carried out in order to eliminate the shortcomings inherent in these electrophotographic elements. In particular, various organic electrophotographic elements have been proposed for that purpose. Among them, multilayer type elements are attracting public attention as electrophotographic elements for use in plain paper copying machines due to their high sensitivity and stable chargeability as compared with usual organic electrophotographic elements, said multilayer type electrophotographic element comprising an electrically conductive substrate, a charge carrier generating layer formed by depositing on said electrically conductive substrate a thin film of organic pigment; and a charge transfer layer formed on said charge carrier generating layer and consisting essentially of a charge transfer material. And, some of them are put to practical use.

As the conventional multilayer type electrophotographic elements of this sort, there are known:

(1) the multilayer type electrophotographic element using, as the charge carrier generating layer, a thin layer formed by vacuum-vapordepositing a perylene derivative and incorporating an oxadiazole derivative in the charge transfer layer (which see U.S. Pat. No. 3,871,882), (2) the multilayer type electrophotographic element using, as the charge carrier generating layer, a thin layer formed by coating an organic amine solution of Chloro Dian Blue and incorporating a hydrazone compound in the charge transfer layer (which see Japanese Patent Publication 42380/1980), (3) the multilayer type electrophotographic element using, as the charge carrier generating layer, a thin layer formed by coating an organic solvent dispersion of distyrylbenzene type disazo compound and incorporating a hydrazone compound in the charge transfer layer (which see Japanese Laid Open Patent Application 84943/1980), and the like.

However, the fact is that even in the multilayer type electrophotographic elements of this sort, the conventional ones have a number of advantages as well as various disadvantages.

That is, the electrophotographic element using the perylene and oxadiazole derivatives disclosed in the preceding (1) is disadvantageous in that the cost of production is raised because the charge carrier generating layer is formed by vacuum vapor-deposition.

The electrophotographic element using the Chloro Dian Blue and hydrazone compound disclosed in the preceding (2) involves disadvantages in the preparation because there is necessity of using a hard-to-handle organic amine (for instance, ethylenediamine) as a coating solvent for the formation of the charge carrier generating layer. Further, this electrophotographic element is inferior in the reproductivity of red images from the original because its visible light wavelengths cover the range of about 450–660 nm. Due to this, it is necessary to employ a filter to cut a red light when this element is actually set in the copying machine, thereby exerting an unprofit influence upon the copying machine design.

The electrophotographic element using the distyrylbenzene type disazo compound and hydrazone compound disclosed in the preceding (3) is very profitable in the preparation because the charge carrier generating layer can be formed readily by coating a dispersion of disazo compound, but is defective, like the electrophotographic element disclosed in the preceding (2), in that the reproductivity of red images from the original is inferior because its sensitive light wavelengths cover the range of about 450–700 nm.

As the disazo compounds used in the multilayer type electrophotographic elements, there are also known, for instance, the benzidine type disazo compound disclosed in Japanese Laid Open Patent Applications 37543/1972 and 55643/1977, the stilbene type disazo compound disclosed in Japanese Laid Open Patent Application 8832/1977 and the like. However, the multilayer type electrophotographic elements using these conventional disazo compounds were generally low in sensitivity and deteriorated in the reproductivity of red images from the original because their sensitive light wavelengths cover the range of about 450–700 nm. Accordingly, these electrophotographic elements were unprofitable in the copying machine design as stated previously, because these elements had to employ a filter to cut a red light when they are actually set in the copying machines.

SUMMARY OF THE INVENTION

It is an object of the present invention to provide a novel tetrazonium salt compound which is capable of producing a variety of disazo compounds used effectively in electrophotographic elements, in particular the above mentioned multilayer type electrophotographic elements.

It is another object of the present invention to provide a novel disazo compound used effectively in electrophotographic elements, in particular the above mentioned multilayer type elements. The multilayer type electrophotographic element using the disazo compound according to the present invention is high in sensitivity as compared with the electrophotographic elements using the conventional disazo compounds, and is also superior in the reproductivity of red images from the original as compared with said conventional electrophotographic elements because the sensitive light wavelength range of the present electrophotographic element is localized only to the short wave length side of the visible light wavelength range (about 450–600 nm).

It is a further object of the present invention is to provide a method of making the above mentioned disazo compound.

It is still a further object of the present invention to provide an electrophotographic element which can be produced readily, is high in sensitivity and is superior in the reproductivity of red images from the original because its sensible light wavelengths are localized in the short wavelength range.

That is, the present invention is primarily directed towards a novel tetrazonium salt compound represented by the following general formula (I):

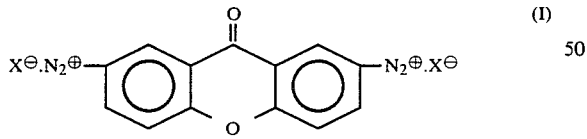

(wherein, X stands for an anion functional group.)

The tetrazonium salt compound represented by the formula (I) is a useful intermediate of the novel disazo compound according to the present invention, which is coupled with proper couplers to synthesize a variety of disazo compounds having xanthone skeletons and azo groups in the 2- and 7-positions thereof. And, this disazo compound is expected to be used as a photoconductive material in the electrophotographic element, in particular a charge carrier generating material.

As the typical anion functional groups in the tetrazonium salt compound represented by the general formula (I), there can be enumerated: $Cl^\ominus$, $Br^\ominus$, $I^\ominus$, $BF_4^\ominus$, $PF_5^\ominus$,

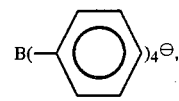

$ClO_4^\ominus$, $SO_4^{2\ominus}$,

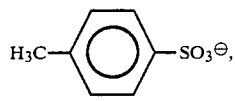

$AsF_6^\ominus$, $SbF_6^\ominus$, preferably $BF_4^\ominus$.

The present invention is secondarily directed towards a novel disazo compound represented by the general formula (II):

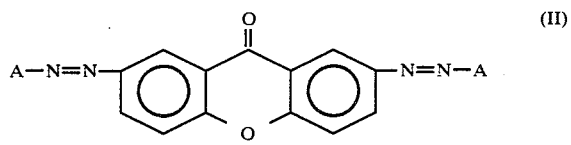

[wherein, A stands for

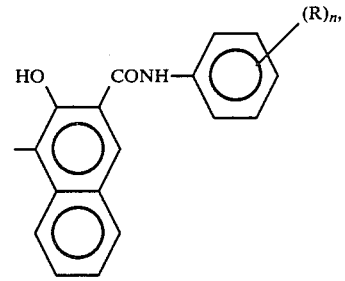

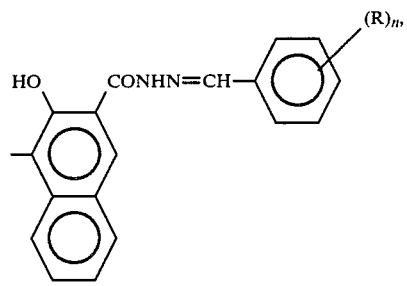

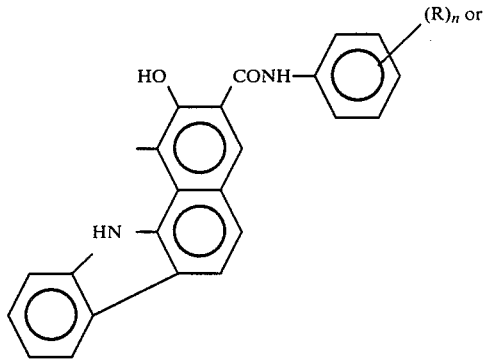

-continued

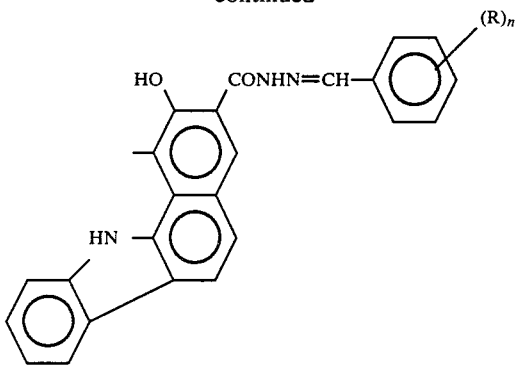

(R stands for an alkyl group such as methyl, ethyl, propyl butyl or the like, an alkoxy group such as methoxy, ethoxy, propoxy, butoxy or the like, a nitro group, halogen, a cyano group or a halomethyl group; n stands for an integer of 0, 1, 2 or 3; and in case n is an integer of 2 or 3, R may be the same or different group.)]

The disazo compound represented by the formula (II) of the present invention, as stated above, is useful as the charge carrier generating material especially in the multilayer type electrophotographic element, and additionally is useful as the charge carrier generating material in the electrophotographic element having the monolayer type photosensitive layer which comprises dispersing the charge carrier generating material and the charge transfer material in a resin and is also useful as the photoconductive material in the electrophotographic element having the photosensitive layer which comprises dispersing the photoconductive material in the resin.

The disazo compounds represented by the general formula (II) are all colored crystals. Next, the typical examples of these disazo compounds will be shown.

| Compound No. | Structural Formula |
|---|---|
| 1 | |
| 2 | |
| 3 | |
| 4 | |
| 8 | |

-continued

| Compound No. | Structural Formula |
|---|---|
| 9 | 3-methoxyphenyl bis-azo compound |
| 10 | 4-methoxyphenyl bis-azo compound |
| 5 | 2-ethylphenyl bis-azo compound |
| 7 | 4-ethylphenyl bis-azo compound |
| 11 | 2-ethoxyphenyl bis-azo compound |
| 12 | 3-ethoxyphenyl bis-azo compound |
| 13 | 4-ethoxyphenyl bis-azo compound |
| 14 | 2-chlorophenyl bis-azo compound |

-continued

| Compound No. | Structural Formula |
|---|---|
| 15 | (2-Cl-C6H4)-NHOC-C6H3(OH)-N=N-C6H3-(C=O)-C6H3(O-)-N=N-C6H3(OH)-CONH-(2-Cl-C6H4), xanthone-type bridge |
| 16 | (4-Cl-C6H4)-NHOC-C6H3(OH)-N=N-C6H3-(C=O)-C6H3(O-)-N=N-C6H3(OH)-CONH-(4-Cl-C6H4) |
| 17 | (2-Br-C6H4)-NHOC-C6H3(OH)-N=N-C6H3-(C=O)-C6H3(O-)-N=N-C6H3(OH)-CONH-(2-Br-C6H4) |
| 18 | (3-Br-C6H4)-NHOC-C6H3(OH)-N=N-C6H3-(C=O)-C6H3(O-)-N=N-C6H3(OH)-CONH-(3-Br-C6H4) |
| 19 | (4-Br-C6H4)-NHOC-C6H3(OH)-N=N-C6H3-(C=O)-C6H3(O-)-N=N-C6H3(OH)-CONH-(4-Br-C6H4) |
| 20 | (2-I-C6H4)-NHOC-C6H3(OH)-N=N-C6H3-(C=O)-C6H3(O-)-N=N-C6H3(OH)-CONH-(2-I-C6H4) |
| 21 | (3-I-C6H4)-NHOC-C6H3(OH)-N=N-C6H3-(C=O)-C6H3(O-)-N=N-C6H3(OH)-CONH-(3-I-C6H4) |
| 23 | (2-F-C6H4)-NHOC-C6H3(OH)-N=N-C6H3-(C=O)-C6H3(O-)-N=N-C6H3(OH)-CONH-(2-F-C6H4) |

| Compound No. | Structural Formula |
|---|---|
| 25 | 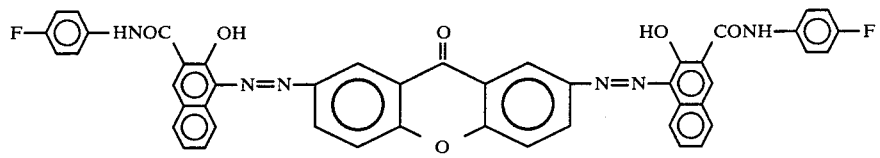 |
| 29 | 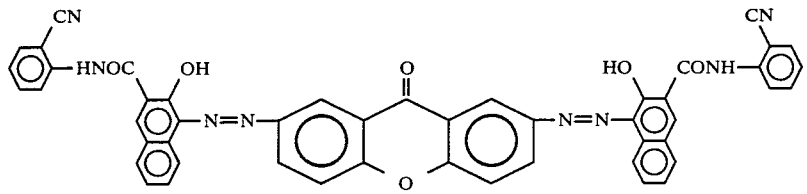 |
| 26 | 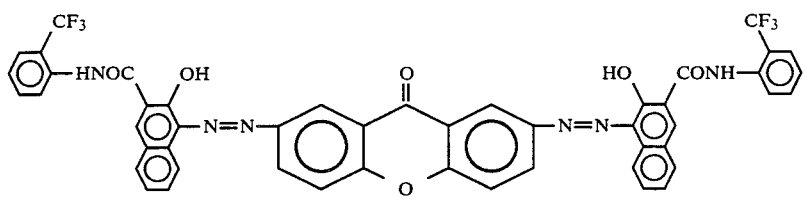 |
| 32 | 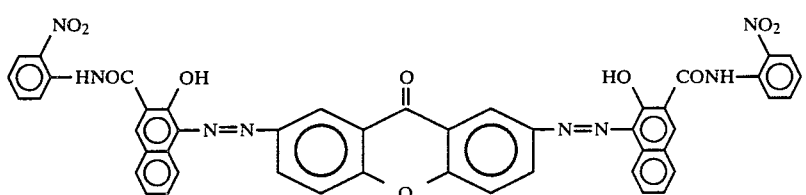 |
| 33 | 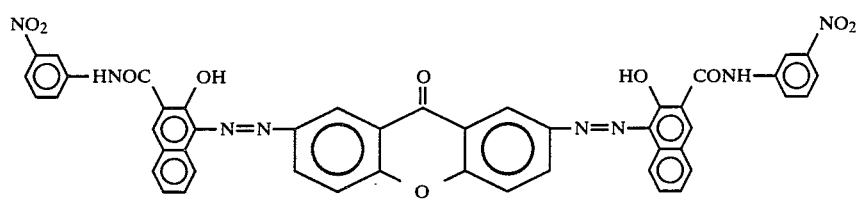 |
| 34 | 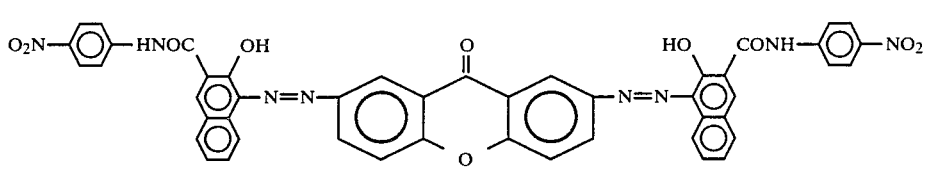 |
| 44 | 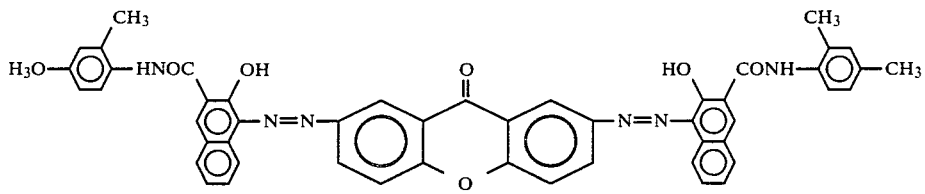 |
| 41 | 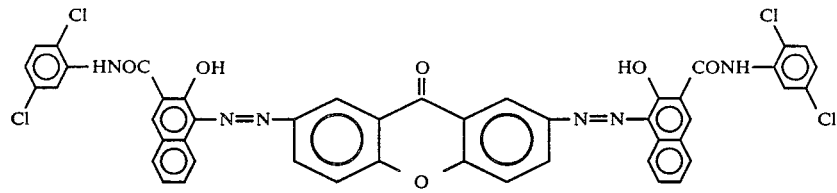 |

| Compound No. | Structural Formula |
|---|---|
| 45 | |
| 77 | |
| 58 | |
| 90 | |
| 84 | |
| 163 | |

| Compound No. | Structural Formula |
|---|---|
| 61 | 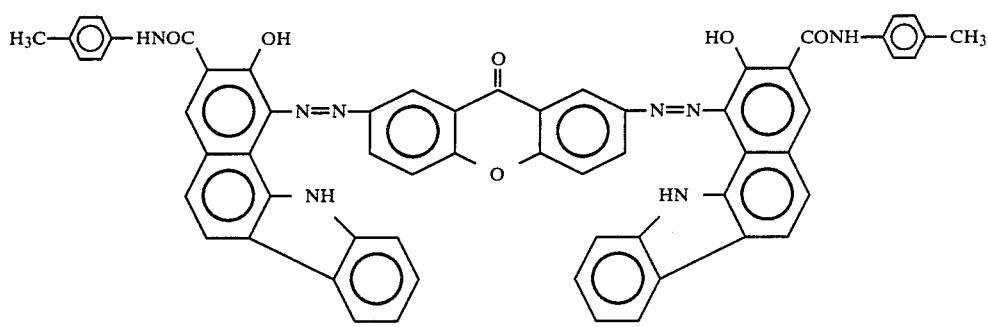 |
| 65 | 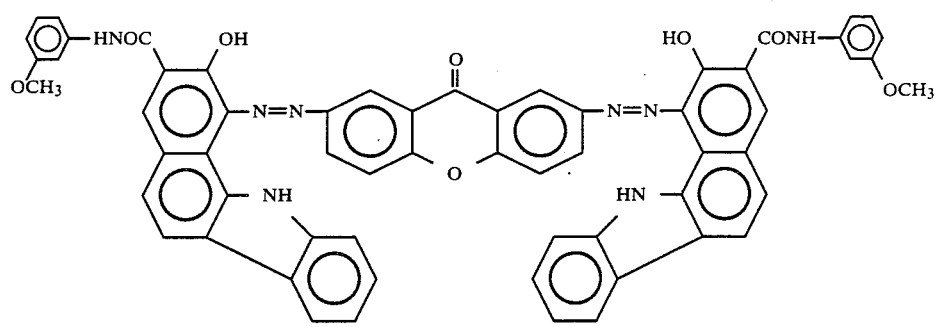 |
| 86 | 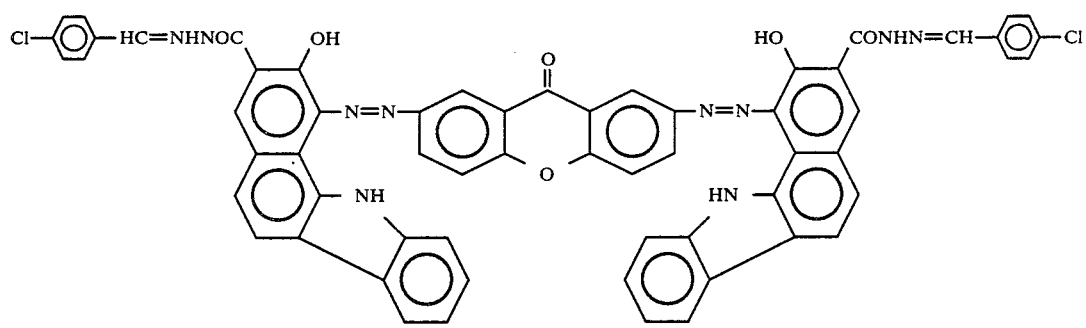 |
| 164 | 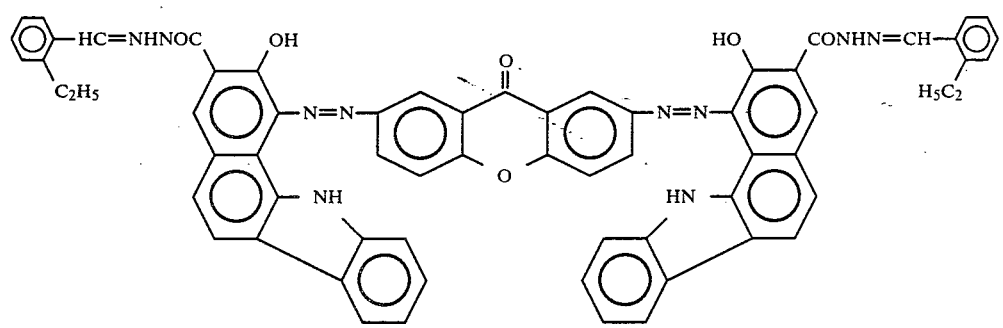 |
The present invention is further directed towards a process for manufacturing a novel disazo compound represented by the general formula (II):
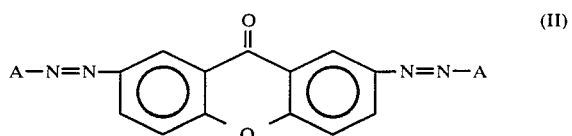

(wherein A is the same defined above) which comprises the steps of diazotating a diamino compound represented by the formula (III):

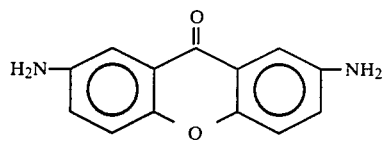
(III)

into tetrazonium salt represented by the general formula (I):

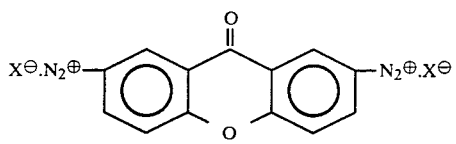
(I)

(wherein X is the same defined above), and then reacting this tetrazonium salt with a compound (which will be called a coupler hereinafter) represented by the general formula (IV), (V), (VI) or (VII):

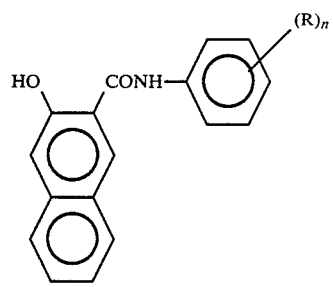
(IV)

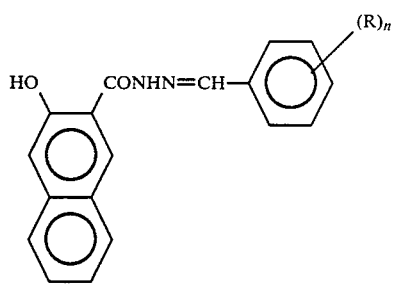
(V)

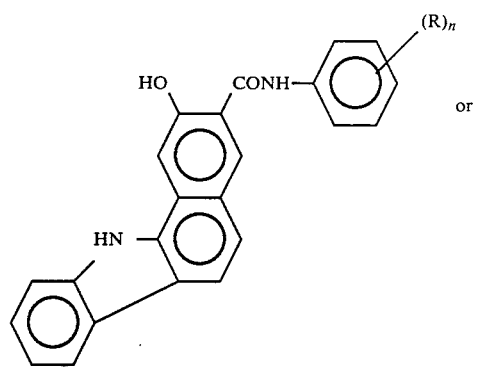
(VI)

or

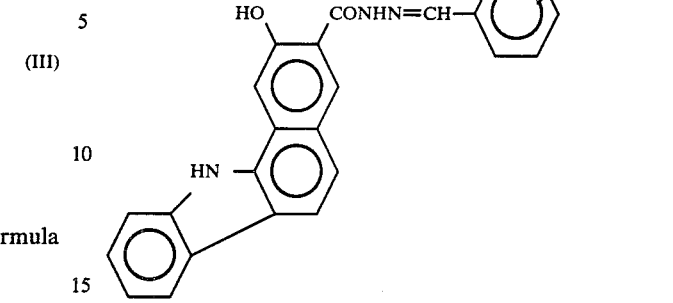
(VII)

(wherein R and n are the same defined above).

The tetrazonium salt represented by the general formula (I) of the present invention can be obtained by reducing, for instance, 2,7-dinitroxanthone into the diamino compound represented by the formula (III), and then diazotating it. In more detail, the process for manufacturing 2,7-dinitroxanthone and 2,7-diaminoxanthone is as described below. For instance, as described in A. A. Goldbery and H. A. Walker, Journal of Chemical Society, 1953, 1348 (1953), 2,7-dinitroxanthone can be obtained by nitrating xanthone in fuming nitric acid, and 2,7-diaminoxanthone can be obtained by reducing 2,7-dinitroxanthone in hydrochloric acid by using a reducing agent such as stannous chloride. The reducing reaction is carried out at a temperature of 95°–100° C. and completed in about 3 hours.

Diazotation of 2,7-diaminoxanthone (III) is carried out by adding sodium nitrite thereto in an inorganic acid such, for instance, as hydrochloric acid or sulfuric acid at a temperature of −10° C. to 20° C. This diazotation reaction is completed in about 30 minutes to 3 hours. Further, by adding for instance borofluoric acid or an aqueous sodium borofluorate solution to this diazotation reaction solution there can be obtained tetrazonium salt.

The preparation of the disazo compound represented by said general formula (II) can also be effected by the action of said diazotation reaction solution per se on a coupler, and further can be effected by the steps of adding for instance borofluoric acid or an aqueous sodium borofluorate solution to the diazotation reaction solution, causing precipitation of tetrazonium salt, isolating the tetrazonium salt, and then making it react with a coupler. Practically, this reaction is carried out by preparing a mixed solution of tetrazonium salt, coupler and an organic solvent such as N,N-dimethylformamide (DMF), dimethyl sulfoxide (DMSO) or the like, and dropping an aqueous alkali solution, for instance, such as an aqueous sodium acetate solution therein at a temperature of about −10° C. to 40° C. This reaction completes in about 5 minutes to 3 hours. After completion of said reaction, separated crystals are filtrated and refined by using a proper way (for instance, washing with water or/and organic solvent, recrystallization or the like). Thus, the preparation of said disazo compound is completed.

The present invention is still further directed towards a multilayer type electrophotographic element comprising an electrically conductive substrate and a photosensitive layer, formed on the substrate, containing a disazo compound represented by the following general formula (VIII) (which will be called sometimes "disazo pigment" hereinafter) as a charge carrier generating material:

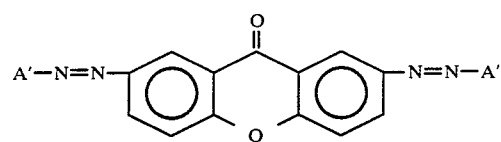 (VIII)

(wherein, A' stands for a coupler group.)

The coupler used in the present invention includes for instance phenolic hydroxyl group-containing compounds such as phenols, naphthols and the like; amino group-containing aromatic amino compounds; or amino group and phenolic hydroxyl group-containing aminonaphthols; aliphatic or aromatic enol form ketone group (active methylene group)-containing compounds, preferably the compounds wherein the coupler group A' is represented by the following general formulas (IX), (X), (XI), (XII), (XIII), (XIV), (XV), (XVI) and (XVII):

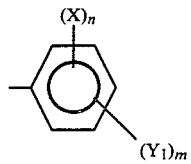 (IX)

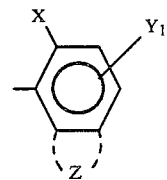 (X)

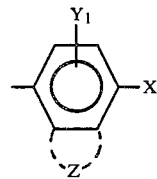 (XI)

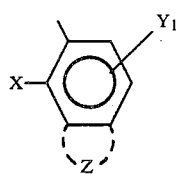 (XII)

[wherein, X, $Y_1$, Z, m and n in the above formulas (IX), (X), (XI) and (XII) each stands for the following:
X:

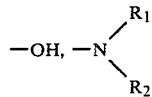

or —NHSO$_2$—R$_3$ (R$_1$ and R$_2$ each stands for hydrogen or a substituted or unsubstituted alkyl group, and R$_3$ stands for a substituted or unsubstituted alkyl group or a substituted or unsubstituted aryl group.)

$Y_1$: hydrogen, halogen, a substituted or unsubstituted alkyl group, a substituted or unsubstituted alkoxy group, a carboxy group, a sulfo group, a substituted or unsubstituted sulfamoyl group, or

(R$_4$ stands for hydrogen, an alkyl group or its substitution product, and a phenyl group or its substitution product, and Y$_2$ stands for a hydrocarbon ring group or its substitution product, a heterocyclic group or its substitution product, of

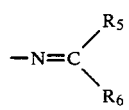

(wherein, R$_5$ stands for a hydrocarbon ring group or its substitution product, a heterocyclic group or its substitution product or a styryl group or its substitution product, R$_6$ stands for hydrogen, an alkyl group, a phenyl group or its substitution product, or R$_5$ and R$_6$ may form a ring in cooperation with carbon atoms bonded thereto.)

Z: a hydrocarbon ring or its substitution product or a heterocyclic ring or its substitution product.]

n: an integer of 1 or 2
m: an integer of 1 or 2

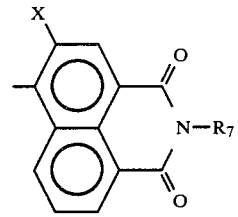 (XIII)

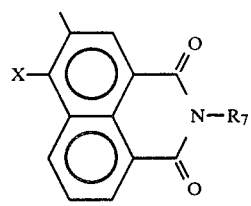 (XIV)

[in the formulas (XIII) and (XIV), R$_7$ stands for a substituted or unsubstituted hydrocarbon group and X is the same as defined above.]

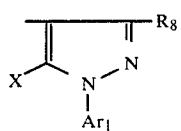 (XV)

[wherein, R$_8$ stands for an alkyl group, a carbamoyl group, a carboxyl group or its ester, Ar$_1$ stands for a hydrocarbon ring group or its substitution product, and X is the same as defined above.]

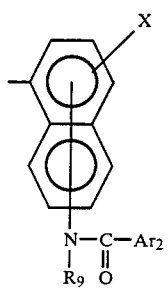 (XVI)

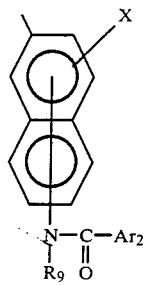 (XVII)

[in the above formulas (XVI) and (XVII), $R_9$ stands for hydrogen or a substituted or unsubstituted hydrocarbon group, and $Ar_2$ stands for a hydrocarbon ring group or its substitution product.]

In said general formula (X), (XI) or (XII), as the hydrocarbon ring there can be enumerated a benzene ring, a naphthalene ring or the like, and as the hetero-ring there can be enumerated an indole ring, a carbazole ring, a benzofuran ring or the like. And, as the substituent on the ring of Z there can be enumerated halogen atoms such as a chlorine atom, a bromine atom and the like.

As the hydrocarbon ring group in $Y_2$ or $R_5$ there can be enumerated a phenyl group, a naphthyl group, an anthryl group, a pyrenyl group and the like, and as the hetero-ring groups there can be enumerated a pyridyl group, a thienyl group, a furyl group, an indolyl group, a benzofuranyl group, a carbazolyl group, a dibenzofuranyl group and the like. Further, as the ring formed by bonding $R_5$ with $R_6$ there can be enumerated a fluorene ring and the like.

As the substituents on the ring formed by the hydrocarbon ring group or hetero-ring group of $Y_2$ or by the cooperation of $R_5$ and $R_6$ there can be enumerated and alkyl group such as a methyl group, an ethyl group, a propyl group, a butyl group or the like, an alkoxy group such as a methoxy group, an ethoxy group, a propoxy group, a butoxy group or the like, a halogen atom such as a chlorine atom a bromine atom or the like, a dialkylamino group such as a dimethylamino group, a diethylamino group or the like, a diaralkylamino group such as a dibenzylamino group or the like, a halomethyl group such as a trifluoromethyl group or the like, a nitro group, a cyano group, a carboxyl group or its ester, a hydroxy group, a sulfonic salt group such as —$SO_3Na$ or the like.

As the substituent on the phenyl group represented by $R_4$ there can be enumerated halogen atoms such as a chlorine atom, a bromine atom or the like.

As the typical examples of the hydrocarbon groups represented by $R_7$ or $R_9$ there can be enumerated an alkyl group such as a methyl group, an ethyl group, a propyl group, a butyl group or the like, an aralkyl group such as a benzyl group or the like, an aryl group such as a phenyl group or the like or esters thereof.

As the substituent on the hydrocarbon group represented by $R_7$ or $R_9$ there can be enumerated an alkyl group such as a methyl group, an ethyl group, a propyl group, a butyl group or the like, an alkoxy group such as a methoxy group, an ethoxy group, a propoxy group, a butoxy group or the like, a halogen atom such as a chlorine atom, a bromine atom or the like, a hydroxyl group, a nitro group or the like.

As the hydrocarbon ring group in $Ar_1$ or $Ar_2$ there can be typically enumerated a phenyl group or a naphthyl group. And, the constituents on these groups include an alkyl group such as a methyl group, an ethyl group, a propyl group, a butyl group or the like, an alkoxy group such as a methoxy group, an ethoxy group, a propoxy group, a butoxy or the like, a nitro group, a halogen atom such as chlorine atom, a bromine atom or the like, a cyano group, a dialkylamino group such as dimethylamino group, a diethylamino group and the like.

Of the couplers represented by X, the hydroxyl group is the most suitable one.

Of the above enumerated coupler groups, the most preferable ones are those belonging to the above mentioned general formulas (X), (XIII), (XIV), (XV), (XVI) and (XVII). Among them, the hydroxyl group belonging to the general formula (X) is preferable. Among them, the coupler group represented by the general formula (XVIII) is preferable:

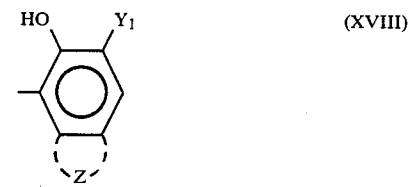 (XVIII)

(wherein, $Y_1$ and Z are the same as defined above.)

More preferable is the one represented by the general formula (XIX):

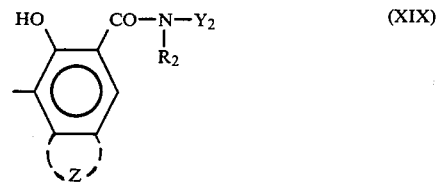 (XIX)

(wherein, Z, $Y_2$ and $R_2$ are same as defined above.)

Still further, among the above mentioned preferable coupler groups, those represented by the general formulas (XX) or (XXI) are suitable:

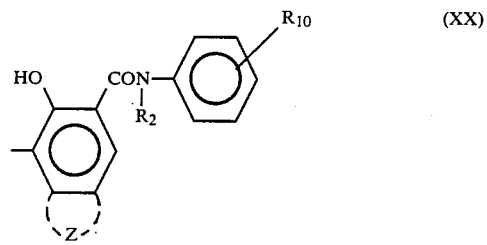 (XX)

-continued

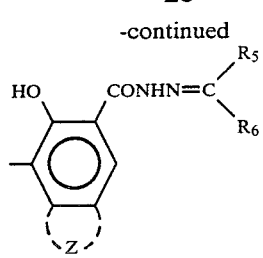
(XXI)

(wherein, Z, $R_2$, $R_5$ and $R_6$ are the same as defined above, and as $R_{10}$ there may be enumerated for instance the above mentioned substituent belonging to $Y_2$.)

The concrete examples of the aforesaid disazo pigments used in the present invention can be shown using structural formulas as follows. For the purpose of simplicity, said structural formulas have been limited only to recite the structural formulas of the coupler groups A' respectively.

| Disazo Pigment No. | A' | Disazo Pigment No. | A' |
|---|---|---|---|
| 1 | 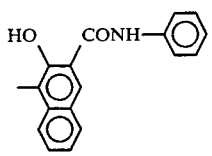 | 2 | 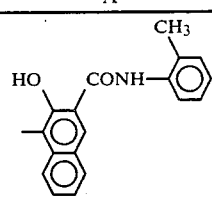 |
| 3 | 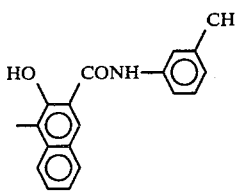 | 4 | 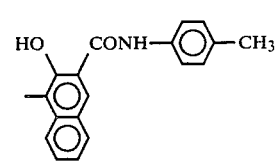 |
| 5 | 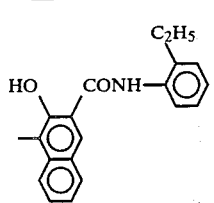 | 6 | 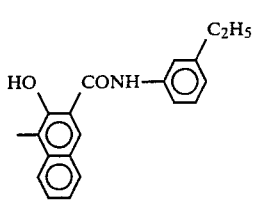 |
| 7 | 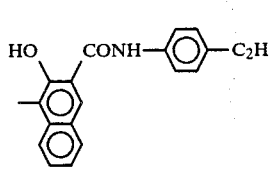 | 8 | 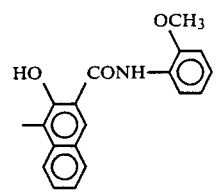 |
| 9 | 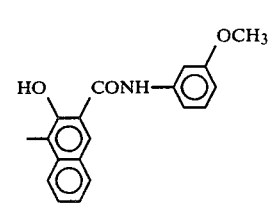 | 10 | 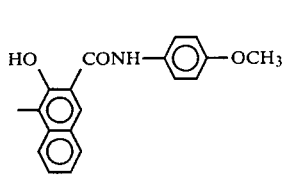 |
| 11 | 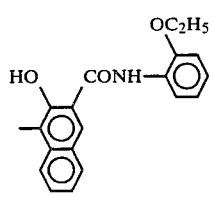 | 12 | 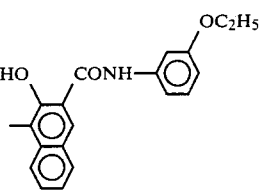 |
| 13 | 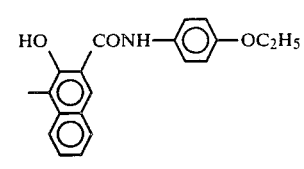 | 14 | 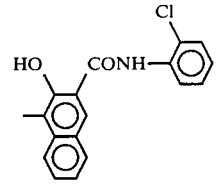 |

-continued

| Disazo Pigment No. | A' | Disazo Pigment No. | A' |
|---|---|---|---|
| 15 | 3-methyl-2-hydroxy-3-naphthoyl-(2-chloroanilide) | 16 | 3-methyl-2-hydroxy-3-naphthoyl-(4-chloroanilide) |
| 17 | 3-methyl-2-hydroxy-3-naphthoyl-(2-bromoanilide) | 18 | 3-methyl-2-hydroxy-3-naphthoyl-(3-bromoanilide) |
| 19 | 3-methyl-2-hydroxy-3-naphthoyl-(4-bromoanilide) | 20 | 3-methyl-2-hydroxy-3-naphthoyl-(2-iodoanilide) |
| 21 | 3-methyl-2-hydroxy-3-naphthoyl-(3-iodoanilide) | 22 | 3-methyl-2-hydroxy-3-naphthoyl-(4-iodoanilide) |
| 23 | 3-methyl-2-hydroxy-3-naphthoyl-(2-fluoroanilide) | 24 | 3-methyl-2-hydroxy-3-naphthoyl-(3-fluoroanilide) |
| 25 | 3-methyl-2-hydroxy-3-naphthoyl-(4-fluoroanilide) | 26 | 3-methyl-2-hydroxy-3-naphthoyl-(2-trifluoromethylanilide) |
| 27 | 3-methyl-2-hydroxy-3-naphthoyl-(3-trifluoromethylanilide) | 28 | 3-methyl-2-hydroxy-3-naphthoyl-(4-trifluoromethylanilide) |
| 29 | 3-methyl-2-hydroxy-3-naphthoyl-(2-cyanoanilide) | 30 | 3-methyl-2-hydroxy-3-naphthoyl-(3-cyanoanilide) |

-continued
| Disazo Pigment No. | A' | Disazo Pigment No. | A' |
|---|---|---|---|
| 31 | 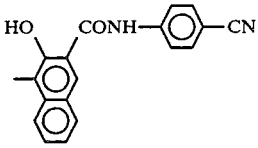 | 32 | 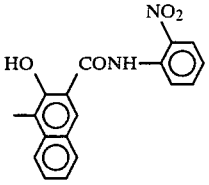 |
| 33 | 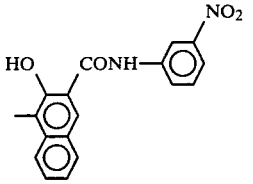 | 34 | 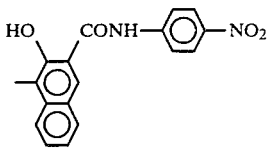 |
| 35 | 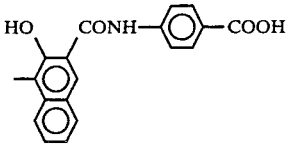 | 36 | 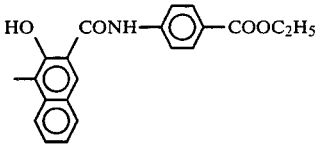 |
| 37 | 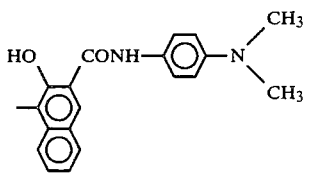 | 38 | 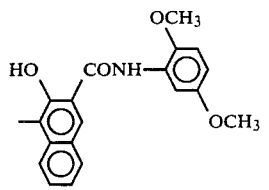 |
| 39 | 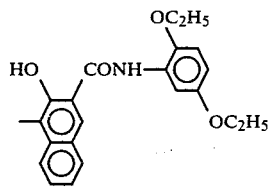 | 40 | 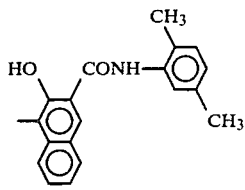 |
| 41 | 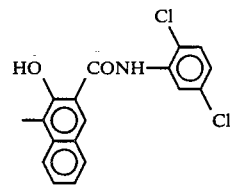 | 42 | 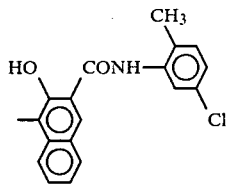 |
| 43 | 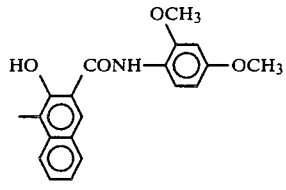 | 44 | 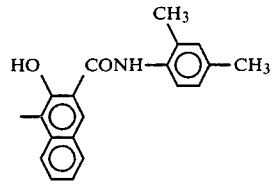 |
| 45 | 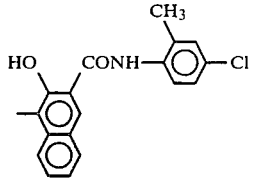 | 46 | 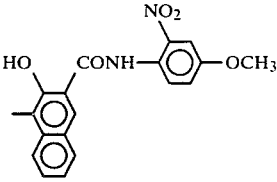 |

-continued

| Disazo Pigment No. | A' | Disazo Pigment No. | A' |
|---|---|---|---|
| 47 | 3-hydroxy-2-methyl-N-(2,5-dimethoxyphenyl)-2-naphthamide | 48 | 3-hydroxy-2-methyl-N-(5-bromo-2-methoxyphenyl)-2-naphthamide |
| 49 | 3-hydroxy-2-methyl-N-(2-methyl-4-methoxyphenyl)-2-naphthamide | 50 | 3-hydroxy-2-methyl-N-(2,5-dimethoxy-4-chlorophenyl)-2-naphthamide |
| 51 | 3-hydroxy-2-methyl-N-(4-sulfonatophenyl)-2-naphthamide (Na salt) | 52 | 3-hydroxy-2-methyl-N-(4-tert-butoxyphenyl)-2-naphthamide |
| 53 | 3-hydroxy-2-methyl-N-(1-naphthyl)-2-naphthamide | 54 | 3-hydroxy-2-methyl-N-(2-naphthyl)-2-naphthamide |
| 55 | 3-hydroxy-2-methyl-N-(2-methoxyphenyl)-6-bromo-2-naphthamide | 56 | 3-hydroxy-2-methyl-N-(2-methylphenyl)-2-anthramide |
| 57 | 3-hydroxy-2-methyl-N-(2-naphthyl)-2-anthramide | 58 | N-phenyl-hydroxycarbazole-carboxamide derivative |
| 59 | N-(2-methylphenyl)-hydroxycarbazole-carboxamide derivative | 60 | N-(3-methylphenyl)-hydroxycarbazole-carboxamide derivative |

*Note: Structural formulas are shown in the original; textual descriptions above approximate the depicted structures.*

-continued

| Disazo Pigment No. | A' | Disazo Pigment No. | A' |
|---|---|---|---|
| 61 | 2-hydroxy-3-methyl-4-(phenylamino)-N-(4-methylphenyl)naphthalene-carboxamide | 62 | 2-hydroxy-3-methyl-4-(phenylamino)-N-(2-ethylphenyl)naphthalene-carboxamide |
| 63 | 2-hydroxy-3-methyl-4-(phenylamino)-N-(4-ethylphenyl)naphthalene-carboxamide | 64 | 2-hydroxy-3-methyl-4-(phenylamino)-N-(2-methoxyphenyl)naphthalene-carboxamide |
| 65 | 2-hydroxy-3-methyl-4-(phenylamino)-N-(3-methoxyphenyl)naphthalene-carboxamide | 66 | 2-hydroxy-3-methyl-4-(phenylamino)-N-(4-methoxyphenyl)naphthalene-carboxamide |
| 67 | 2-hydroxy-3-methyl-4-(phenylamino)-N-(2-ethoxyphenyl)naphthalene-carboxamide | 68 | 2-hydroxy-3-methyl-4-(phenylamino)-N-(3-ethoxyphenyl)naphthalene-carboxamide |
| 69 | 2-hydroxy-3-methyl-4-(phenylamino)-N-(4-ethoxyphenyl)naphthalene-carboxamide | 70 | 2-hydroxy-3-methyl-4-(phenylamino)-N-(2-chlorophenyl)naphthalene-carboxamide |
| 71 | 2-hydroxy-3-methyl-4-(phenylamino)-N-(3-chlorophenyl)naphthalene-carboxamide | 72 | 2-hydroxy-3-methyl-4-(phenylamino)-N-(4-chlorophenyl)naphthalene-carboxamide |

-continued

| Disazo Pigment No. | A' | Disazo Pigment No. | A' |
|---|---|---|---|
| 73 | 2-hydroxy-3-methyl-4-(phenylamino)-N-(2-nitrophenyl)naphthalene-2-carboxamide | 74 | 2-hydroxy-3-methyl-4-(phenylamino)-N-(3-nitrophenyl)naphthalene-2-carboxamide |
| 75 | 2-hydroxy-3-methyl-4-(phenylamino)-N-(4-nitrophenyl)naphthalene-2-carboxamide | 76 | 2-hydroxy-3-methyl-4-(phenylamino)-N-(2-methyl-4-methoxyphenyl)naphthalene-2-carboxamide |
| 77 | 2-hydroxy-3-methylnaphthalene-2-carbohydrazide (benzylidene) | 78 | 2-hydroxy-3-methylnaphthalene-2-carbohydrazide (2-methylbenzylidene) |
| 79 | 2-hydroxy-3-methylnaphthalene-2-carbohydrazide (3-methylbenzylidene) | 80 | 2-hydroxy-3-methylnaphthalene-2-carbohydrazide (4-methylbenzylidene) |
| 81 | 2-hydroxy-3-methylnaphthalene-2-carbohydrazide (2-methoxybenzylidene) | 82 | 2-hydroxy-3-methylnaphthalene-2-carbohydrazide (3-methoxybenzylidene) |
| 83 | 2-hydroxy-3-methylnaphthalene-2-carbohydrazide (4-methoxybenzylidene) | 84 | 2-hydroxy-3-methylnaphthalene-2-carbohydrazide (2-chlorobenzylidene) |
| 85 | 2-hydroxy-3-methylnaphthalene-2-carbohydrazide (3-chlorobenzylidene) | 86 | 2-hydroxy-3-methylnaphthalene-2-carbohydrazide (4-chlorobenzylidene) |

-continued

| Disazo Pigment No. | A' | Disazo Pigment No. | A' |
|---|---|---|---|
| 87 | 3-hydroxy-2-methylnaphthalene-CONHN=CH-(2-NO₂-phenyl) | 88 | 3-hydroxy-2-methylnaphthalene-CONHN=CH-(3-NO₂-phenyl) |
| 89 | 3-hydroxy-2-methylnaphthalene-CONHN=CH-(4-NO₂-phenyl) | 90 | 3-hydroxy-2-methyl-4-(phenylamino)naphthalene-CONHN=CH-phenyl |
| 91 | 3-hydroxy-2-methyl-4-(phenylamino)naphthalene-CONHN=CH-(2-CH₃-phenyl) | 92 | 3-hydroxy-2-methyl-4-(phenylamino)naphthalene-CONHN=CH-(3-CH₃-phenyl) |
| 93 | 3-hydroxy-2-methyl-4-(phenylamino)naphthalene-CONHN=CH-(4-CH₃-phenyl) | 94 | 3-hydroxy-2-methyl-4-(phenylamino)naphthalene-CONHN=CH-(2-OCH₃-phenyl) |
| 95 | 3-hydroxy-2-methyl-4-(phenylamino)naphthalene-CONHN=CH-(3-OCH₃-phenyl) | 96 | 3-hydroxy-2-methyl-4-(phenylamino)naphthalene-CONHN=CH-(4-OCH₃-phenyl) |
| 97 | 3-hydroxy-2-methyl-4-(phenylamino)naphthalene-CONHN=CH-(2-Cl-phenyl) | 98 | 3-hydroxy-2-methyl-4-(phenylamino)naphthalene-CONHN=CH-(3-Cl-phenyl) |

-continued

| Disazo Pigment No. | A' | Disazo Pigment No. | A' |
|---|---|---|---|
| 99 | (structure: 2-hydroxy-3-methyl-4-phenylamino-naphthalene with CONHN=CH–C₆H₄–Cl) | 100 | (structure: 2-hydroxy-3-methyl-4-phenylamino-naphthalene with CONHN=CH–C₆H₄–NO₂, ortho) |
| 101 | (structure: 2-hydroxy-3-methyl-4-phenylamino-naphthalene with CONHN=CH–C₆H₄–NO₂, meta) | 102 | (structure: 2-hydroxy-3-methyl-4-phenylamino-naphthalene with CONHN=CH–C₆H₄–NO₂, para) |
| 103 | (structure: 3-hydroxy-2-methylnaphthalene with CONHN=CH–anthracenyl) | 104 | (structure: 3-hydroxy-2-methylnaphthalene with CONHN=CH–(N-ethylcarbazol-3-yl)) |
| 105 | (structure: 3-hydroxy-2-methylnaphthalene with CONHN=CH–thienyl) | 106 | (structure: 3-hydroxy-2-methylnaphthalene with CONH–(3-methoxydibenzofuran-2-yl)) |
| 107 | (structure: 3-hydroxy-2-methylnaphthalene with CONH–(carbazol-3-yl)) | 108 | (structure: 3-hydroxy-2-methylnaphthalene with CON(CH₃)–phenyl) |
| 109 | (structure: 3-hydroxy-2-methylnaphthalene with CON(phenyl)₂) | 110 | (structure: 3-hydroxy-2-methylnaphthalene with CON(CH₃)–(2-methylphenyl)) |
| 111 | (structure: 3-hydroxy-2-methylnaphthalene with CON(C₂H₅)–(4-methoxyphenyl)) | 112 | (structure: 3-hydroxy-2-methylnaphthalene with CON(4-chlorophenyl)₂) |

-continued

| Disazo Pigment No. | A' | Disazo Pigment No. | A' |
|---|---|---|---|
| 113 | 2-hydroxy-3-methyl-N-(4-chlorophenyl)carbamoyl with fused NH-phenyl ring | 114 | 2-hydroxy-3-methyl-N-(2,5-dimethoxyphenyl)carbamoyl with fused O-phenyl ring |
| 115 | naphthalimide, 4-HO, 5-CH₃, N—CH₃ | 116 | naphthalimide, 4-HO, 5-CH₃, N—C₂H₅ |
| 117 | naphthalimide, 4-HO, 5-CH₃, N—C₃H₇ | 118 | naphthalimide, 4-HO, 5-CH₃, N—C₂H₄OCH₃ |
| 119 | naphthalimide, 5-HO, 4-CH₃, N—CH₃ | 120 | naphthalimide, 5-HO, 4-CH₃, N—C₂H₅ |
| 121 | naphthalimide, 5-HO, 4-CH₃, N—C₃H₇ | 122 | naphthalimide, 5-HO, 4-CH₃, N—C₂H₄OCH₃ |
| 123 | 3-methyl-1-phenyl-5-hydroxypyrazole | 124 | 3-methyl-1-(4-nitrophenyl)-5-hydroxypyrazole |
| 125 | 3-methyl-1-(4-sulfophenyl)-5-hydroxypyrazole | 126 | 3-methyl-1-(2,3,5-trichloro-6-sulfophenyl)-5-hydroxypyrazole |

-continued

| Disazo Pigment No. | A' | Disazo Pigment No. | A' |
|---|---|---|---|
| 127 | 3-methyl-1-(4-methylphenyl)-5-hydroxypyrazole | 128 | 3-methyl-1-(4-methoxyphenyl)-5-hydroxypyrazole |
| 129 | 3-methyl-1-(4-chlorophenyl)-5-hydroxypyrazole | 130 | 3-methyl-1-(2,4-dinitrophenyl)-5-hydroxypyrazole |
| 131 | 3-methyl-1-(4-cyanophenyl)-5-hydroxypyrazole | 132 | 3-methyl-1-(4-dimethylaminophenyl)-5-hydroxypyrazole |
| 133 | 1-(4-methoxyphenyl)-5-hydroxypyrazole-3-carboxylic acid | 134 | ethyl 1-phenyl-5-hydroxypyrazole-3-carboxylate |
| 135 | N-(2-hydroxy-3-methylnaphthalen-1-yl)-4-chlorobenzamide | 136 | N-(2-hydroxy-3-methylnaphthalen-1-yl)-1-naphthamide |
| 137 | N-(2-hydroxy-3-methylnaphthalen-1-yl)-4-dimethylaminobenzamide | 138 | N-(2-hydroxy-3-methylnaphthalen-1-yl)-4-nitrobenzamide |
| 139 | N-(2-hydroxy-3-methylnaphthalen-1-yl)-3-nitrobenzamide | 140 | N-(2-hydroxy-3-methylnaphthalen-1-yl)-3-methylbenzamide |

-continued
| Disazo Pigment No. | A' | Disazo Pigment No. | A' |
|---|---|---|---|
| 141 | 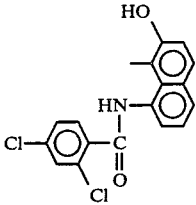 | 142 | 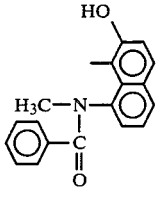 |
| 143 | 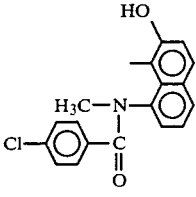 | 144 | 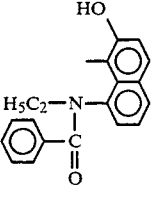 |
| 145 | 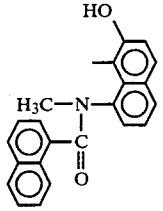 | 146 | 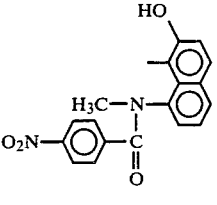 |
| 147 | 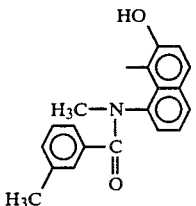 | 148 | 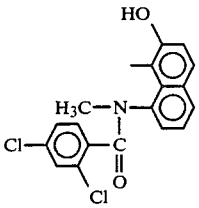 |
| 149 | 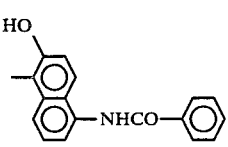 | 150 | 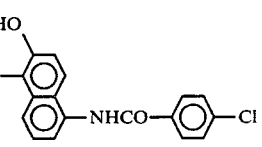 |
| 151 | 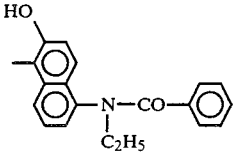 | 152 | 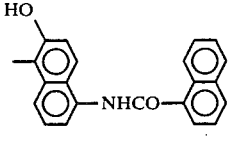 |
| 153 | 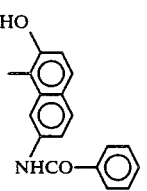 | 154 | 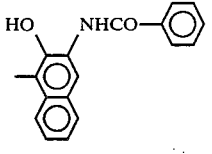 |
| 155 | 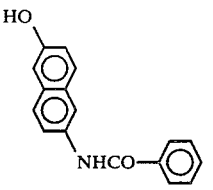 | 156 | 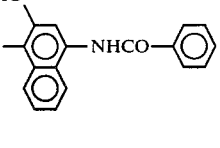 |

-continued

| Disazo Pigment No. | A' | Disazo Pigment No. | A' |
|---|---|---|---|
| 157 | | 158 | |
| 159 | | 160 | |
| 161 | | 162 | |
| 163 | | 164 | |

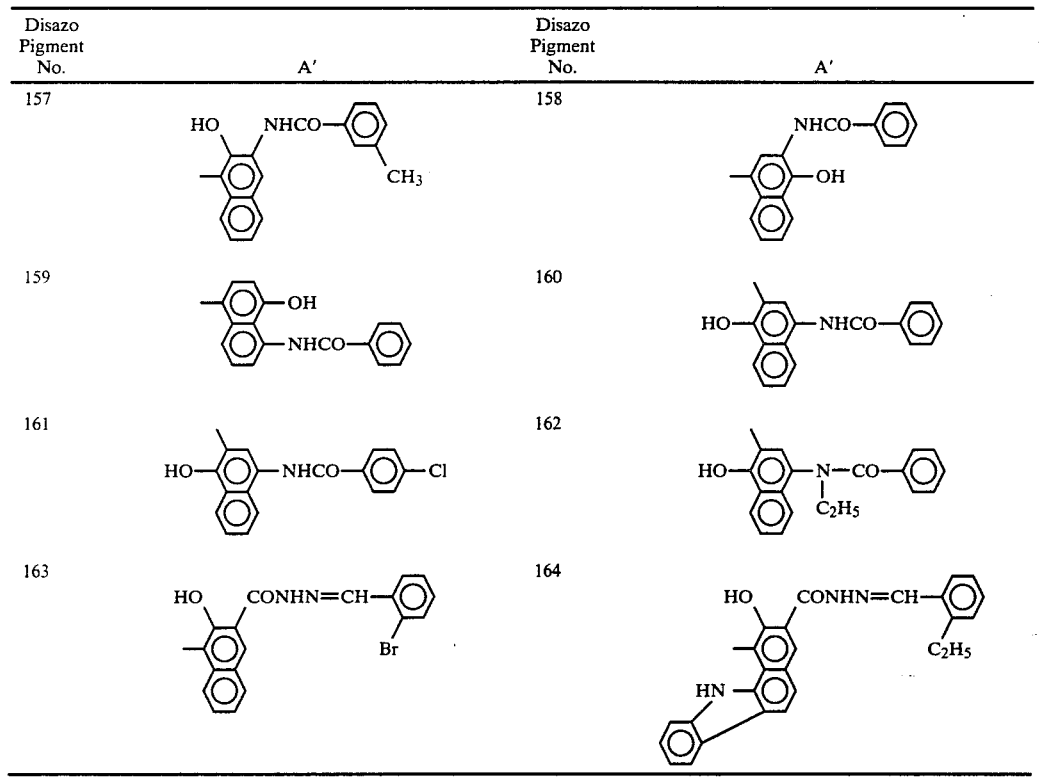

The use of above mentioned disazo compounds according to the present invention can readily produce extremely high-sensitive electrophotographic elements. Among them, Disazo compound Nos. 14, 17, 20, 23, 26, 29, 58, 84 and 90 are especially preferable.

These disazo compounds can be prepared according to the exactly same procedure as described above. That is, said disazo compounds can be readily prepared by diazotating 2,7-diaminoxanthone in a normal manner to thereby obtain tetrazonium salt, and then subjecting this salt and couplers corresponding thereto, to a coupling reaction in a proper solvent such, for instance, as N,N-dimethyl-formamide under the influence of a base.

In the electrophotographic element according to the present invention, the disazo compound is used as the charge carrier generating material in the photosensitive layer. The typical construction of this electrophotographic element was shown in FIG. 3 and FIG. 4.

Figure 3:
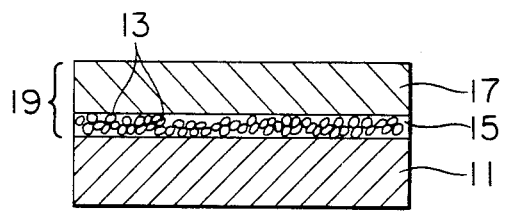

The electrophotographic element shown in FIG. 3 is the one comprising an electrically conductive substrate 11 and a multilayer type photosensitive layer 19, formed on said substrate, which comprises a charge carrier generating layer 15 consisting essentially of a disazo compound 13 and a charge transfer layer 17 consisting essentially of a charge transfer compound and an insulating binder.

In the electrophotographic element shown in FIG. 3, the imagewise irradiate transmits through the charge transfer layer and reaches the charge carrier generating layer 15 where charge carriers are generated by the aid of disazo compound 13 contained therein, while the charge transfer layer 17 is injected with charge carriers and transfers them. That is, the said electrophotographic element has such a mechanism that the disazo compound 13 takes part in generating charge carriers required for light decay and the charge transfer 17 takes part in transferring said charge carriers.

Figure 4:
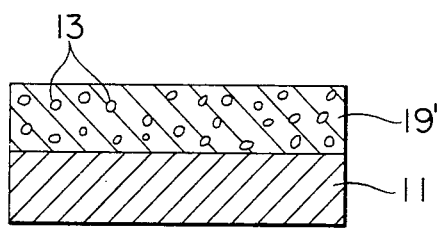
Figure 5:
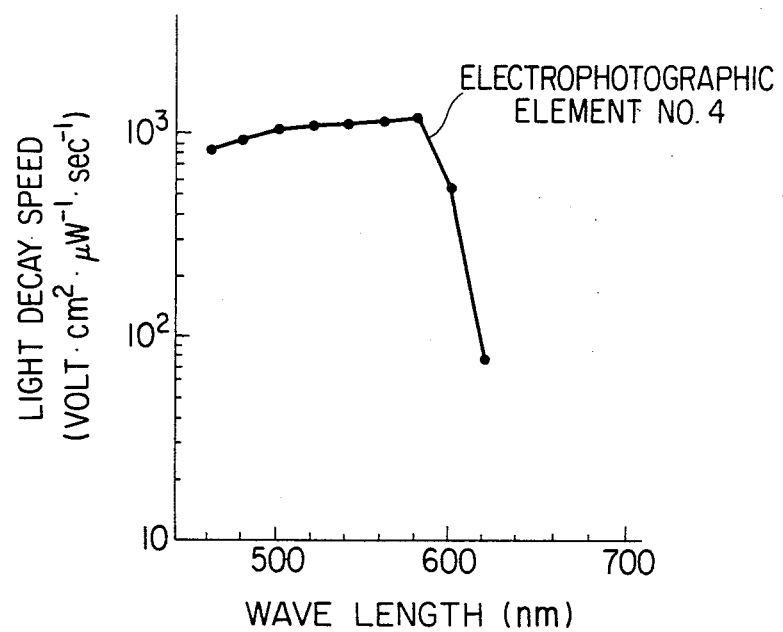
Figure 6:
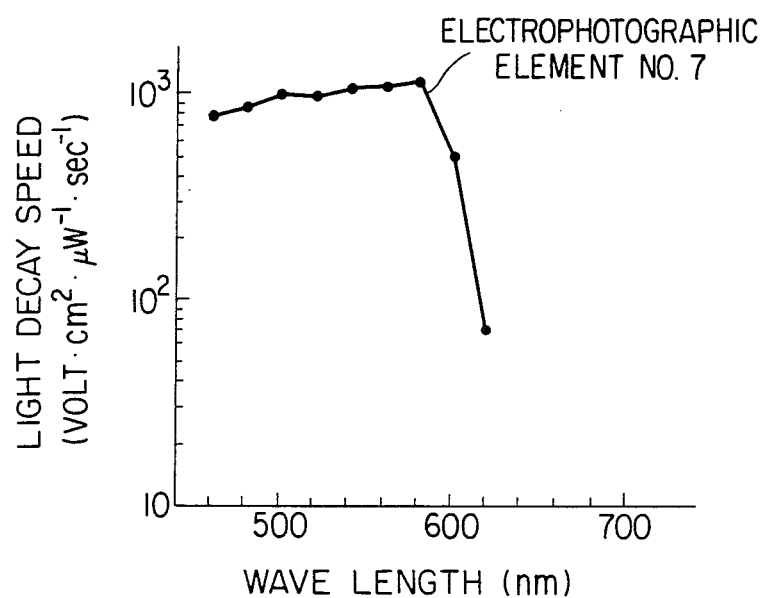
Figure 7:
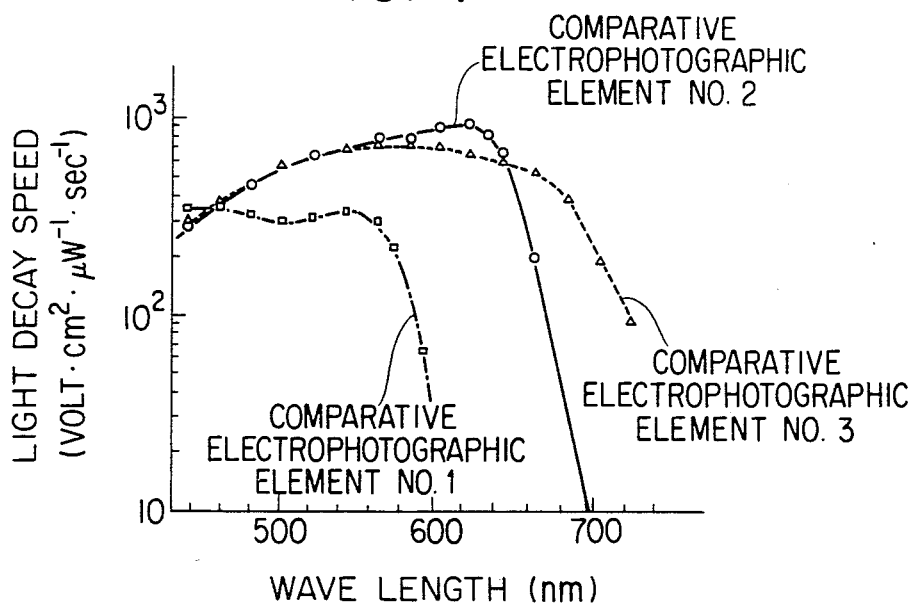

The electrophotographic element shown in FIG. 4 comprises an electrically conductive substrate 11 and a monolayer type photosensitive layer 19, formed on said substrate, which is consisted essentially of a disazo compound 13, a charge transfer material and an insulating binder, wherein said disazo compound 13 is a charge carrier generating material. As another electrophotographic element, there can be enumerated the one obtained by reversing the order of the charge carrier generating layer and the charge transfer layer in the electrophotographic element of FIG. 3.

In the photosensitive layer of FIG. 3, the charge carrier generating layer 15 is preferably 0.01 to $5\mu$ thick, more preferably 0.05 to $2\mu$. In case this thickness is less than 0.01, charge carriers are not generated to the full, while in case this thickness is more than $5\mu$, the residual electric potential is too high to be used practically. The thickness of the charge transfer layer 17 is preferably 3 to $50\mu$, more preferably 5 to $20\mu$. In case this thickness is less than $3\mu$, the chargeability is insufficient, while the said thickness is more than $50\mu$, the residual electric potential is too high to be used practically. The charge carrier generating layer 15 is consisted essentially of the disazo compound represented by the above mentioned general formula and further can contain a binder, a plasticizer and the like. The percentage of the disazo compound in the charge carrier generating is preferably 30 to 100 wt.%, more preferably 50 wt.% or more. The charge transfer layer 17 is consisted essentially of a charge transfer material and a binder, and may further contain a plasticizer and the like. The percentage of the charge transfer material in the charge transfer layer is 10 to 95 wt.%, preferably 30 to 90 wt.%. In case the percentage occupied by the

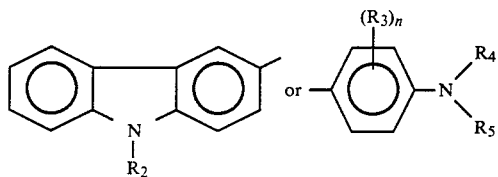

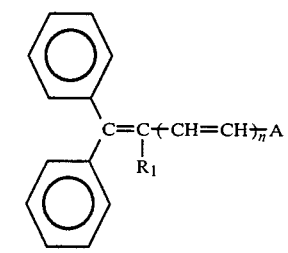

(10)

R₂ stands for an alkyl group having 1 to 4 carbon atoms, R₃ stands for hydrogen, halogen, an alkyl group having 1 to 4 carbon atoms, an alkoxy group or a dialkylamino group having 1 to 4 carbon atoms, n stands for an integer of 1 or 2 and in case n is 2 R₃ may be the same or different, and R₄ and R₅ stand for hydrogen, and a substituted or unsubstituted alkyl or benzyl group.)

[wherein, n stands for an integer of 0 or 1, R₁ stands for a hydrogen atom, an alkyl group or a substituted or unsubstituted phenyl group, A stands for

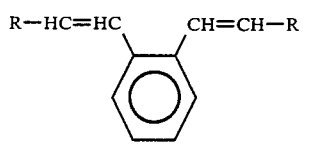

(7)

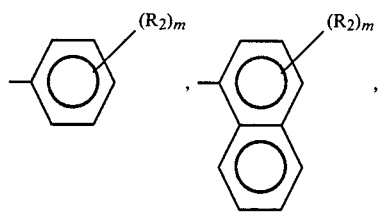

(wherein, R stands for a carbazolyl group, a pyridyl group, a thienyl group, an indolyl group, a furyl group or each substituted or unsubstituted phenyl group, styryl group, naphthyl group or anthryl group, each substituent being one member selected from the group consisting of a dialkylamino group, an alkyl group, an alkoxy group, a carboxy group or their esters, a halogen atom, a cyano group, an aralkyl amino group, an N-alkyl-N aralkyl amino group, an amino group, a nitro group and an acetylamino group.)

9-anthryl group or a substituted or unsubstituted N-alkylcarbazolyl group, R₂ stands for a hydrogen atom, an alkyl group, an alkoxy group, a halogen atom or

(wherein, R₃ and R₄ each stands for an alkyl group, a substituted or unsubstituted aralkyl group, a substituted or unsubstituted aryl group, and R₃ and R₄ may form a ring), m stands for an integer of 0, 1, 2 or 3, and in case m is more than 2 R₂ may be the same or different.]

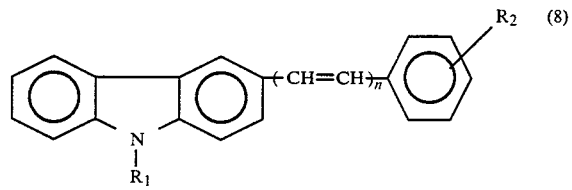

(8)

(wherein, R₁ stands for a lower alkyl group or a benzyl group, R₂ stands for a hydrogen atom, a lower alkyl group, a lower alkoxy group, a halogen atom, a nitro group, an amino group or a lower alkyl group or a benzyl substituted amino group, and n is an integer of 1 or 2.)

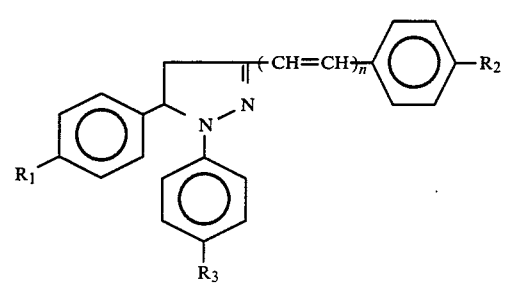

11.

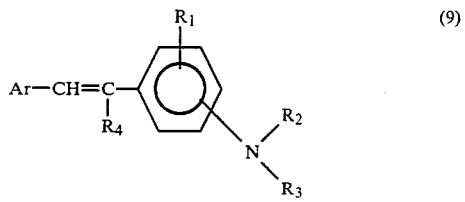

(9)

(wherein, R₁ stands for a hydrogen atom, an alkyl group, an alkoxy group or a halogen atom, R₂ and R₃ each stands for an alkyl group, a substituted or unsubstituted aralkyl group or a substituted or unsubstituted aryl group, R₄ stands for a hydrogen atom or a substituted or unsubstituted phenyl group, and Ar stands for a phenyl group or a naphthyl group.)

(wherein, R₁, R₂ and R₃ each stands for hydrogen, a lower alkyl group, a lower alkoxy group, a dialkylamino group or a halogen atom, and n stands for an integer of 0 or 1.)

The compounds represented by the general formula (I) include for instance 9-ethylcarbazole-3-aldehyde-1-methyl-1-phenyl-hydrazone, 9-ethylcarbazole-3-aldehyde-1-benzyl-1-phenylhydrazone, 9-ethylcarbazole-3-aldehyde-1,1-diphenylhydrazone and the like. The compounds represented by the general formula (2) include for instance 4-diethylaminostyrene-β-aldehyde-1-methyl-1-phenylhydrazone, 4-methoxynaphthalene-1-aldehyde-1-benzyl-1-phenylhydrazone and the like. The compounds represented by the general formula (3) include for instance 4-methoxybenzaldehyde-1-methyl-1-

PREFERRED EMBODIMENTS OF THE INVENTION

Next, the present invention will be explained concretely with reference to Examples, but the present invention should not be limited thereto.

EXAMPLE 1 (PREPARATION OF THE TETRAZONIUM SALT)

29.18 g of 2,7-diaminoxanthone was added to a diluted hydrochloric acid comprising 224 ml of water and 224 ml of concentrated hydrochloric acid. This maxture was heated at about 60° C. for 1 hour and then cooled to $-3°$ C. In succession, a solution obtained by dissolving 18.7 g of sodium nitrite in 90 ml of water was dropped in the thus treated mixture at a temperature of $-3°$ C. to 0° C. for 50 minutes. Thereafter, the same was stirred at the same temperature for 30 minutes, and then 150 ml of 42% borofluoric acid was added to this reaction solution. Separated crystals were filtrated, washed with water and dried to thereby obtain 47.13 g (yield: 86.1%) of pale yellow crystals of tetrazonium fluoroborate. This compound was observed to have a decomposition point of 145° C. or more, show the infrared absorption spectrum (KBr tablet method) as illustrated in FIG. 1, and have an absorption band caused by $N_2^{\oplus}$ at 2280 $cm^{-1}$ and an absorption band caused by $>C=O$ at 1685 $cm^{-1}$.

EXAMPLE 2 [PREPARATION OF THE DISAZO COMPOUND ACCORDING TO THE FORMULA (II)]

50 g of the tetrazonium salt obtained according to Example 1 and 6.25 g of 2-hydroxy-3-naphthoic acid anilide (whose moles are twice as large as those of tetrazonium salt) which acts as a coupler, were dissolved in 700 ml of cooled, N,N-dimethyl formamide. A solution comprising 4.0 g of sodium acetate and 35 ml of water was dropped therein at a temperature of 5° to 10° C. for 20 minutes, and after the stop of cooling, the mixture was further stirred at room temperature for 3 hours. Subsequently, the formed precipitates were filtered out, washed 3 times with 700 ml of N,N-dimethyl formamide heated to 80° C., next washed 2 times with 700 ml of water, and dried at 80° C. at a reduced pressure of 2 mmHg to obtain 8.2 g (yield 90.0%) of No. 1 disazo compound. This disazo compound looks red powder externally.

Figure 2:
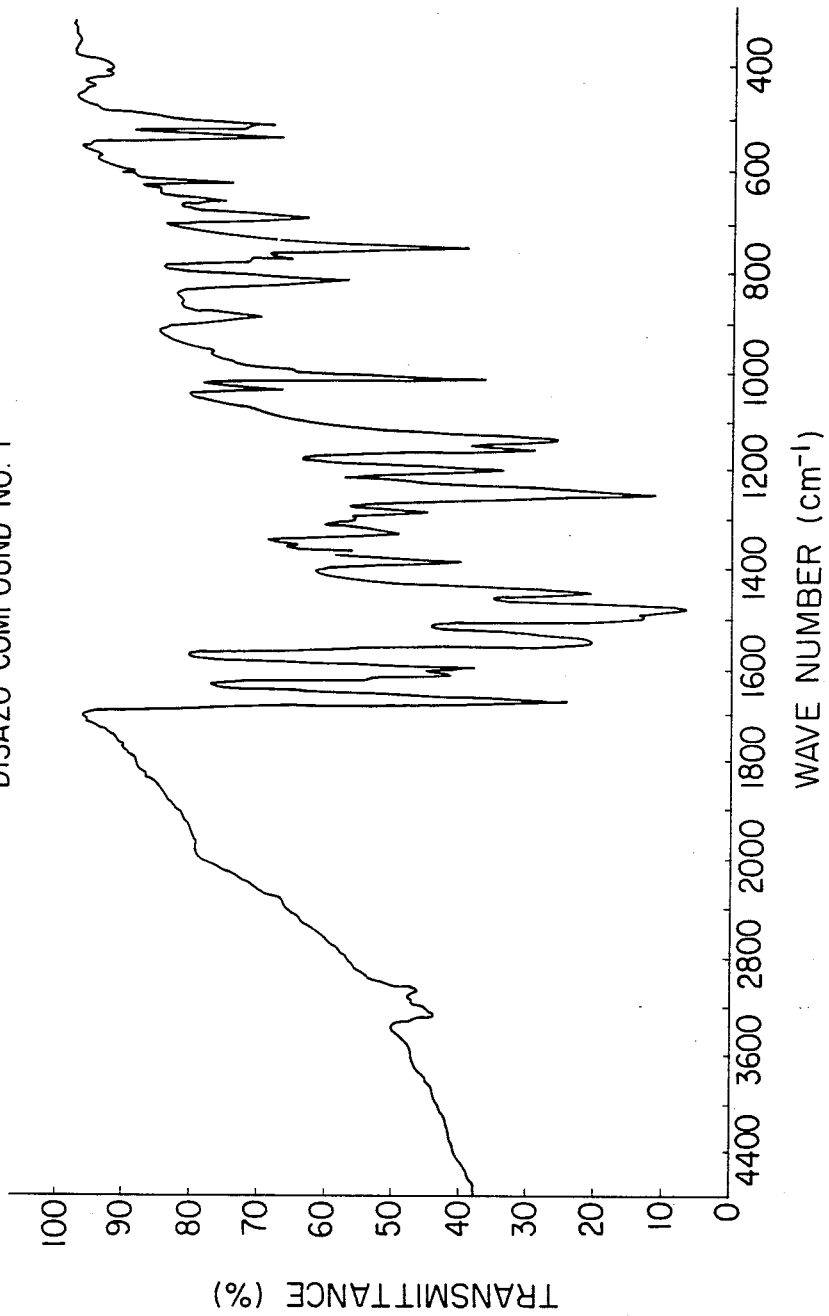

Its infrared spectrum (KBr tablet method) was shown in FIG. 2.

EXAMPLE 3 TO EXAMPLE 40 [PREPARATION OF DISAZO COMPOUNDS OF THE FORMULA (II)]

Disazo compounds according to the formula (II) were prepared by repeating the exactly same procedure as Example 1 except that the following compounds shown in Table 1 were as couplers.

TABLE-1

| Example No. | Compound No. | Coupler | Yield (%) (appearance) |
|---|---|---|---|
| 3 | 2 | HO–[naphthyl]–CONH–[phenyl with CH₃ ortho] | 87.6 (red) |
| 4 | 3 | HO–[naphthyl]–CONH–[phenyl with CH₃ meta] | 93.4 (red) |
| 5 | 4 | HO–[naphthyl]–CONH–[phenyl]–CH₃ (para) | 84.4 (red) |

TABLE-1-continued
| Example No. | Compound No. | Coupl | Yield (%) (appearance) |
|---|---|---|---|
| 11 | 11 | 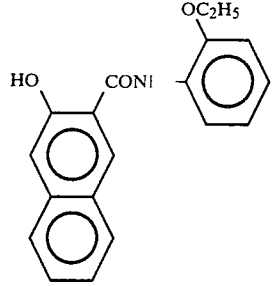 | 91.4 (red) |
| 12 | 12 | 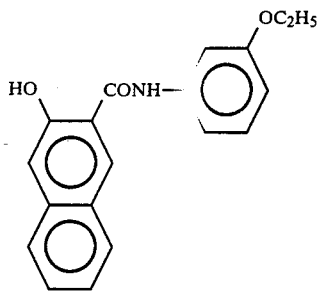 | 91.8 (red) |
| 13 | 13 | 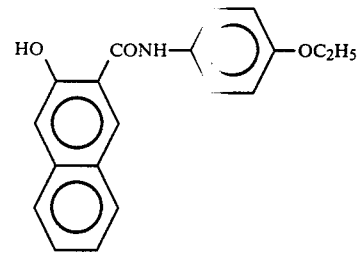 | 76.1 (red) |
| 14 | 14 | 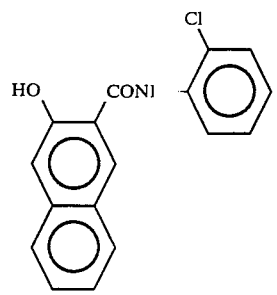 | 83.4 (red) |
| 15 | 15 | 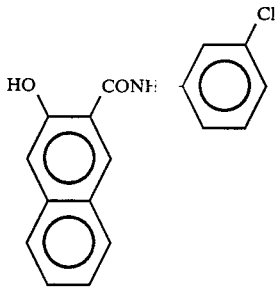 | 81.9 (red) |

TABLE-1-continued

| Example No. | Compound No. | Coupler | Yield (%) (appearance) |
|---|---|---|---|
| 21 | 21 | 3-hydroxy-N-(3-iodophenyl)-2-naphthamide | 85.5 (red) |
| 22 | 23 | 3-hydroxy-N-(2-fluorophenyl)-2-naphthamide | 81.5 (red) |
| 23 | 25 | 3-hydroxy-N-(4-fluorophenyl)-2-naphthamide | 78.1 (red) |
| 24 | 29 | 3-hydroxy-N-(2-cyanophenyl)-2-naphthamide | 82.5 (red) |
| 25 | 26 | 3-hydroxy-N-(2-trifluoromethylphenyl)-2-naphthamide | 86.3 (red) |

TABLE-1-continued
| Example No. | Compound No. | Coupler | Yield (%) (appearance) |
|---|---|---|---|
| 31 | 45 | 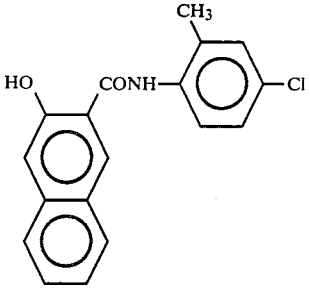 | 80.0 (red) |
| 32 | 77 | 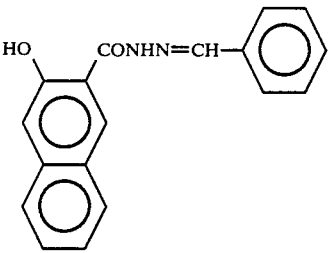 | 92.0 (red) |
| 33 | 58 | 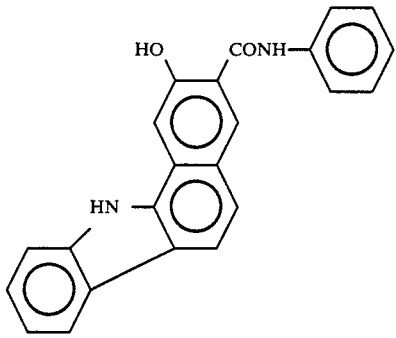 | 82.0 (dark red) |
| 34 | 90 | 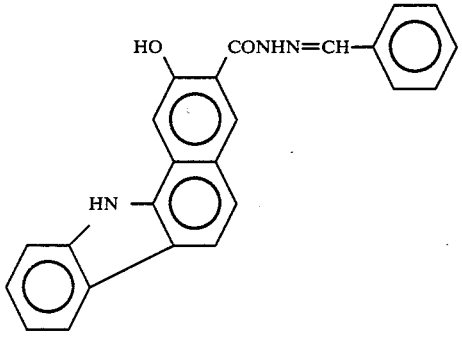 | 65.1 (dark red) |
| 35 | 84 | 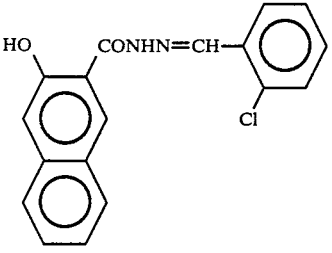 | 85.0 (red) |

TABLE-1-continued

| Example No. | Compound No. | Coupler | Yield (%) (appearance) |
|---|---|---|---|
| 40 | 164 | (structure: HO, CONHN=CH–phenyl with H₅C₂; naphthol fused with HN–indole) | 71.1 (dark red) |

And, the data such as melting points, elementary analysis values and infrared absorption spectrums of the thus obtained disazo compounds were shown in the following Table-2.

TABLE 2

| Example No. | Compound No. | Melting Point | Element | Elementary Analysis Value Calculated value (%) | Measured Value (%) | IR Absorption Spectrum (KBr disc) $\nu_{c=0}$ (cm$^{-1}$) |
|---|---|---|---|---|---|---|
| 2 | 1 | 300° C. or more | C | 72.86 | 72.61 | 1675 |
|   |   |   | H | 3.91 | 3.88 |   |
|   |   |   | N | 10.84 | 10.77 |   |
| 3 | 2 | 300° C. or more | C | 73.30 | 73.12 | 1675 |
|   |   |   | H | 4.28 | 4.27 |   |
|   |   |   | N | 10.46 | 10.44 |   |
| 4 | 3 | 300° C. or more | C | 73.30 | 73.04 | 1670 |
|   |   |   | H | 4.28 | 4.30 |   |
|   |   |   | N | 10.46 | 10.46 |   |
| 5 | 4 | 300° C. or more | C | 73.30 | 73.41 | 1665 |
|   |   |   | H | 4.28 | 4.25 |   |
|   |   |   | N | 10.46 | 10.46 |   |
| 6 | 8 | 300° C. or more | C | 70.49 | 70.25 | 1670 |
|   |   |   | H | 4.11 | 4.02 |   |
|   |   |   | N | 10.06 | 9.97 |   |
| 7 | 9 | 300° C. or more | C | 70.49 | 70.21 | 1675 |
|   |   |   | H | 4.11 | 4.07 |   |
|   |   |   | N | 10.06 | 9.97 |   |
| 8 | 10 | 300° C. or more | C | 70.49 | 70.28 | 1670 |
|   |   |   | H | 4.11 | 4.01 |   |
|   |   |   | N | 10.06 | 9.99 |   |
| 9 | 5 | 300° C. or more | C | 73.72 | 73.67 | 1670 |
|   |   |   | H | 4.62 | 4.55 |   |
|   |   |   | N | 9.99 | 10.09 |   |
| 10 | 7 | 300° C. or more | C | 73.72 | 73.58 | 1670 |
|   |   |   | H | 4.62 | 4.53 |   |
|   |   |   | N | 9.99 | 10.10 |   |
| 11 | 11 | 300° C. or more | C | 70.98 | 71.02 | 1665 |
|   |   |   | H | 4.45 | 4.34 |   |
|   |   |   | N | 9.73 | 9.82 |   |
| 12 | 12 | 300° C. or more | C | 70.98 | 70.91 | 1670 |
|   |   |   | H | 4.45 | 4.32 |   |
|   |   |   | N | 9.73 | 9.71 |   |
| 13 | 13 | 300° C. or more | C | 70.98 | 70.74 | 1665 |
|   |   |   | H | 4.45 | 4.33 |   |
|   |   |   | N | 9.73 | 9.60 |   |
| 14 | 14 | 300° C. or more | C | 66.91 | 66.89 | 1675 |
|   |   |   | H | 3.35 | 3.43 |   |
|   |   |   | N | 9.96 | 9.92 |   |
| 15 | 15 | 300° C. or more | C | 66.91 | 66.70 | 1670 |
|   |   |   | H | 3.35 | 3.29 |   |
|   |   |   | N | 9.96 | 9.90 |   |
| 16 | 16 | 300° C. or more | C | 66.91 | 66.83 | 1675 |
|   |   |   | H | 3.35 | 3.42 |   |
|   |   |   | N | 9.96 | 10.08 |   |
| 17 | 17 | 300° C. or more | C | 60.53 | 60.27 | 1675 |
|   |   |   | H | 3.03 | 2.84 |   |
|   |   |   | N | 9.01 | 8.91 |   |
| 18 | 18 | 300° C. or more | C | 60.53 | 60.43 | 1670 |
|   |   |   | H | 3.03 | 2.80 |   |
|   |   |   | N | 9.01 | 8.96 |   | by weight of polycarbonate resin (Panlite-K-1300: produced by TEIJIN K.K.) and 16 parts by weight of tetrahydrofuran by means of a doctor blade. The same was airdried, whereby an about 1 μm-thick charge carrier generating layer was formed.

Then, a solution obtained by mixing and dissolving 2 parts by weight of 9-ethylcarbazole-3-aldehyde-1-methyl-1-phenylhydrazone (charge transfer material), 2 parts by weight of polycarbonate resin (Panlite K-1300: produced by TEIJIN K.K.) and 16 parts by weight of tetrahydrofuran was applied on this charge carrier generating layer by means of a doctor blade, was dried at 80° C. for 2 minutes and in succession was dried at 105° C. for 5 minutes, thereby forming an about 20 μm-thick charge transfer layer. Thus, there was prepared a multilayer type electrophotographic element No. 1 shown in FIG. 3.

EXAMPLE 42 TO EXAMPLE 66

Electrophotographic element No. 2 to No. 26 were prepared by repeating the exactly same procedure as Example 41 except that the disazo compound No. 1 used in Example 41 was replaced by the disazo compound shown in Table-3 referred to afterwards.

EXAMPLE 67 TO EXAMPLE 87

Electrophotographic element No. 27 to No. 47 were prepared by repeating the exactly same procedure as Example 41 except that 1-phenyl-3-(4-diethylaminostyryl)-5-(4-diethylaminophenyl)pyrazolone was used as the charge transfer material and the disazo compounds shown in Table 4 referred to afterwards were used.

EXAMPLE 88 TO EXAMPLE 106

Electrophotographic element No. 48 to No. 66 were prepared by repeating the exactly same procedure as Example 41 except that 9-(4-diethylaminostyryl)anthracene was used as the charge transfer material and the disazo compound shown in Table-5 referred to afterwards.

EXAMPLE 107 TO EXAMPLE 114

Electrophotographic element No. 67 to No. 74 were prepared by repeating the exactly same procedure as Example 41 except that 1,1-bis(4-dibenzylaminophenyl)propane was used as the charge transfer material and the disazo compound shown in Table-6 referred to afterwards was used.

These electrophotographic elements No. 1 to No. 74 were subjected to −6 KV corona discharge for 20 seconds by means of an electrostatic copying paper tester (SP428 Type: produced by Kawaguchi Electro Works) and charged negatively. Thereafter these electrophotographic elements were left standing in the dark for 20 seconds to measure the surface potential Vpo(V) at that time. In succession, said elements were exposed to radiation of light from a tungsten lamp so that the intensity of illumination on their surfaces might be 4.5 lux. and, the time (second) required until the surface potential was reduced to ½ of Vpo was found out and the exposure amount E½ (lux.sec) was calculated therefrom on each element. The thus obtained results were shown in Table-3–Table-6.

TABLE 3

| Example No. | Electrophotographic Element No. | Disazo Compound No. | Vpo (volt) | E½ (lux · sec) |
|---|---|---|---|---|
| 41 | 1 | 1 | 1009 | 12.5 |
| 42 | 2 | 2 | 465 | 4.0 |
| 43 | 3 | 8 | 252 | 9.7 |
| 44 | 4 | 14 | 1319 | 2.3 |
| 45 | 5 | 15 | 1260 | 7.9 |
| 46 | 6 | 16 | 852 | 6.2 |
| 47 | 7 | 17 | 1227 | 2.4 |
| 48 | 8 | 18 | 1224 | 4.7 |
| 49 | 9 | 19 | 780 | 8.3 |
| 50 | 10 | 20 | 1211 | 2.7 |
| 51 | 11 | 21 | 1163 | 7.5 |
| 52 | 12 | 22 | 749 | 9.2 |
| 53 | 13 | 23 | 1301 | 3.1 |
| 54 | 14 | 24 | 1215 | 8.5 |
| 55 | 15 | 25 | 830 | 9.0 |
| 56 | 16 | 26 | 1195 | 6.5 |
| 57 | 17 | 27 | 928 | 9.9 |
| 58 | 18 | 29 | 1241 | 8.8 |
| 59 | 19 | 30 | 721 | 12.1 |
| 60 | 20 | 32 | 1270 | 9.9 |
| 61 | 21 | 58 | 738 | 2.0 |
| 62 | 22 | 62 | 922 | 4.8 |
| 63 | 23 | 84 | 1238 | 3.9 |
| 64 | 24 | 85 | 1141 | 8.3 |
| 65 | 25 | 90 | 1140 | 1.3 |
| 66 | 26 | 93 | 1208 | 3.9 |

TABLE 4

| Example No. | Electrophotographic Element No. | Disazo Compound No. | Vpo (volt) | E½ (lux · sec) |
|---|---|---|---|---|
| 67 | 27 | 1 | 1009 | 12.5 |
| 68 | 28 | 2 | 465 | 4.0 |
| 69 | 29 | 3 | 1082 | 13.2 |
| 70 | 30 | 4 | 916 | 8.2 |
| 71 | 31 | 5 | 948 | 15.2 |
| 72 | 32 | 6 | 237 | 5.7 |
| 73 | 33 | 14 | 1123 | 2.2 |
| 74 | 34 | 15 | 1044 | 9.9 |
| 75 | 35 | 17 | 1227 | 2.4 |
| 76 | 36 | 18 | 1045 | 5.5 |
| 77 | 37 | 20 | 1151 | 3.0 |
| 78 | 31 | 21 | 1022 | 8.5 |
| 79 | 39 | 23 | 1198 | 3.3 |
| 80 | 40 | 24 | 995 | 9.1 |
| 81 | 41 | 26 | 1244 | 7.1 |
| 82 | 42 | 29 | 1176 | 7.8 |
| 83 | 43 | 32 | 1235 | 8.2 |
| 84 | 44 | 58 | 208 | 0.8 |
| 85 | 45 | 84 | 1250 | 4.1 |
| 86 | 46 | 87 | 1100 | 10.5 |
| 87 | 47 | 94 | 1095 | 5.5 |

TABLE 5

| Example No. | Electrophotographic Element No. | Disazo Compound No. | Vpo (volt) | E½ (lux · sec) |
|---|---|---|---|---|
| 88 | 48 | 2 | 1436 | 13.9 |
| 89 | 49 | 3 | 1145 | 15.0 |
| 90 | 50 | 4 | 1233 | 19.1 |
| 91 | 51 | 7 | 884 | 13.7 |
| 92 | 52 | 14 | 1240 | 2.9 |
| 93 | 53 | 15 | 1258 | 11.8 |
| 94 | 54 | 16 | 1526 | 10.5 |
| 95 | 55 | 17 | 1121 | 2.9 |
| 96 | 56 | 18 | 1164 | 6.1 |
| 97 | 57 | 19 | 1406 | 18.4 |
| 98 | 58 | 20 | 1310 | 3.5 |
| 99 | 59 | 23 | 1227 | 4.3 |
| 100 | 60 | 32 | 1338 | 18.4 |
| 101 | 61 | 33 | 1085 | 10.9 |
| 102 | 62 | 34 | 1246 | 5.7 |
| 103 | 63 | 58 | 940 | 2.3 |
| 104 | 64 | 84 | 1195 | 3.9 | trophotographic elements according to the present invention are high in sensitivity and their sensitive wavelengths cover about 460 to 600 nm.

Further, Electrophotographic Element No. 4 and No. 7 of the present invention were each subjected to 10,000 time-repeated reproduction by means of a copying machine RICOPY-P-500 manufactured by RICOH COMPANY, LTD.

As the result, each electrophotographic element was found to produce a clear-cut image without any change caused by repetition of copying processes. It may be understood therefrom that the electrophotographic elements of the present invention are also superior in durability.

I claim:

1. An electrophotographic element comprising an electrically conductive substrate and a photosensitive layer, formed on said substrate, which is consisted essentially of a disazo compound as a charge carrier generating material represented by the general formula (VIII):

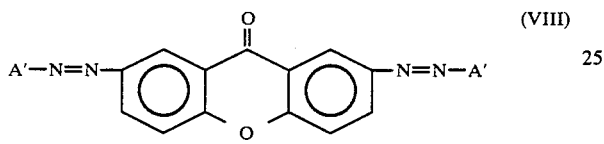

(wherein, A' stands for a coupler group.), a charge transfer material and an insulating binder.

2. An element according to claim 1 wherein A' in the general formula (VIII) is selected from the group of structural formulas represented by the following (IX), (X), (XI), (XII), (XIII), (XIV), (XV), (XVI) and (XVII) [wherein, in the above mentioned formulas, namely

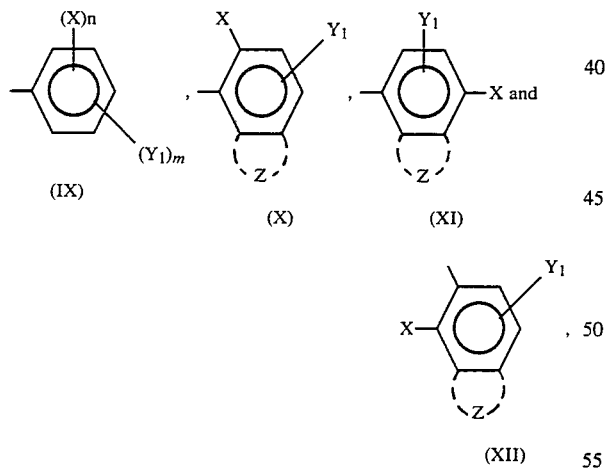

X, Y$_1$, Z, m and n each stands for the following matters:

X:

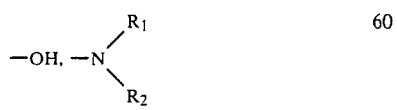

or —NHSO$_2$—R$_3$ (R$_1$ and R$_2$ each stands for hydrogen or a substituted or unsubstituted alkyl group, and R$_3$ stands for a substituted or unsubstituted alkyl group or a substituted or unsubstituted aryl group.)

Y$_1$: hydrogen, halogen, a substituted or unsubstituted alkyl group, a substituted or unsubstituted alkoxy group, a carboxy group, a sulfogroup, a substituted or unsubstituted sulfamoyl group or

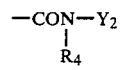

[R$_4$ stands for hydrogen, an alkyl group or its substitution product, and a phenyl group or its substitution product, and Y$_2$ stands for a hydrocarbon ring group or its substitution product or a heterocyclic group or its substitution product or

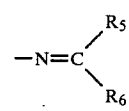

(wherein, R$_5$ stands for a hydrocarbon cyclic group or its substitution product, a heterocyclic group or its substitution product or a styryl group or its substitution product, R$_6$ stands for hydrogen, an alkyl group, a phenyl group or its substitution product, or R$_5$ and R$_6$ may form a ring together with carbon atoms bonded thereto.)]

Z: a hydrocarbon ring or its substitution product or a heterocyclic ring or its substitution product n: an integer of 1 or 2 m: an integer of 1 or 2

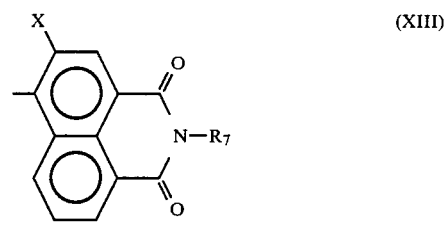

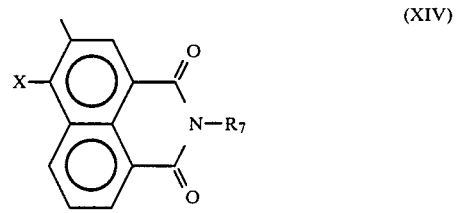

[in the formulas (XIII) and (XIV), R$_7$ stands for a substituted or unsubstituted hydrocarbon group and X is the same as defined above.]

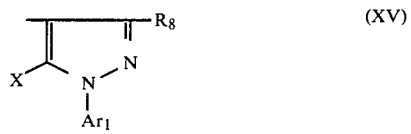

[wherein, R$_8$ stands for an alkyl group, a carbamoyl group, a carboxyl group or its ester, Ar$_1$ stands for a hydrocarbon ring group or its substitution product, and X is the same as defined above.]

trophotographic elements according to the present invention are high in sensitivity and their sensitive wavelengths cover about 460 to 600 nm.

Further, Electrophotographic Element No. 4 and No. 7 of the present invention were each subjected to 10,000 time-repeated reproduction by means of a copying machine RICOPY-P-500 manufactured by RICOH COMPANY, LTD.

As the result, each electrophotographic element was found to produce a clear-cut image without any change caused by repetition of copying processes. It may be understood therefrom that the electrophotographic elements of the present invention are also superior in durability.

I claim:

1. An electrophotographic element comprising an electrically conductive substrate and a photosensitive layer, formed on said substrate, which is consisted essentially of a disazo compound as a charge carrier generating material represented by the general formula (VIII):

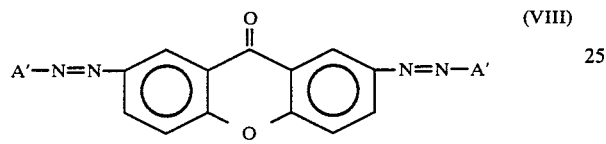

(wherein, A' stands for a coupler group.), a charge transfer material and an insulating binder.

2. An element according to claim 1 wherein A' in the general formula (VIII) is selected from the group of structural formulas represented by the following (IX), (X), (XI), (XII), (XIII), (XIV), (XV), (XVI) and (XVII) [wherein, in the above mentioned formulas, namely

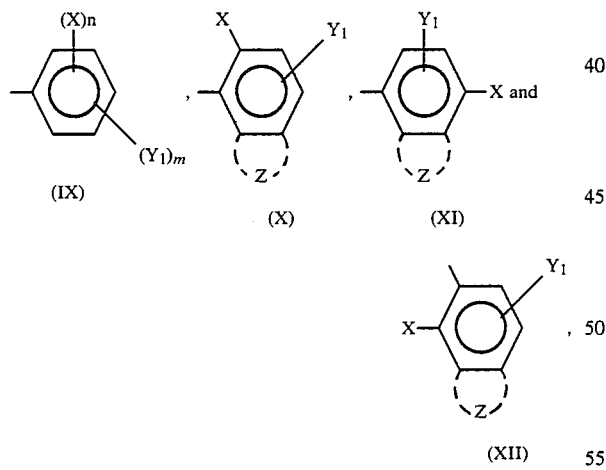

X, Y₁, Z, m and n each stands for the following matters:

X:

or —NHSO₂—R₃ (R₁ and R₂ each stands for hydrogen or a substituted or unsubstituted alkyl group, and R₃ stands for a substituted or unsubstituted alkyl group or a substituted or unsubstituted aryl group.)

Y₁: hydrogen, halogen, a substituted or unsubstituted alkyl group, a substituted or unsubstituted alkoxy group, a carboxy group, a sulfogroup, a substituted or unsubstituted sulfamoyl group or

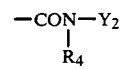

[R₄ stands for hydrogen, an alkyl group or its substitution product, and a phenyl group or its substitution product, and Y₂ stands for a hydrocarbon ring group or its substitution product or a heterocyclic group or its substitution product or

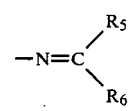

(wherein, R₅ stands for a hydrocarbon cyclic group or its substitution product, a heterocyclic group or its substitution product or a styryl group or its substitution product, R₆ stands for hydrogen, an alkyl group, a phenyl group or its substitution product, or R₅ and R₆ may form a ring together with carbon atoms bonded thereto.)]

Z: a hydrocarbon ring or its substitution product or a heterocyclic ring or its substitution product n: an integer of 1 or 2 m: an integer of 1 or 2

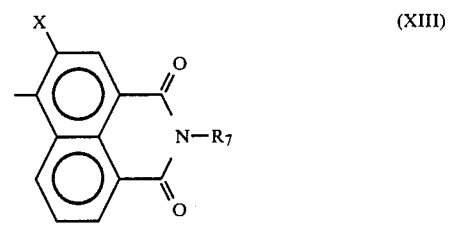

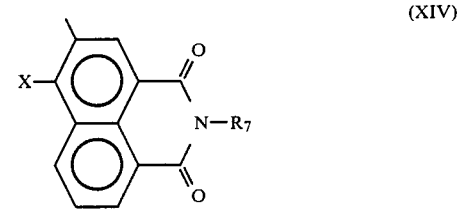

[in the formulas (XIII) and (XIV), R₇ stands for a substituted or unsubstituted hydrocarbon group and X is the same as defined above.]

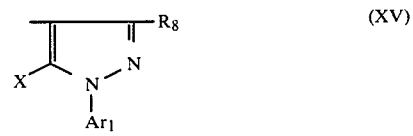

[wherein, R₈ stands for an alkyl group, a carbamoyl group, a carboxyl group or its ester, Ar₁ stands for a hydrocarbon ring group or its substitution product, and X is the same as defined above.]

TABLE-1-continued

| Example No. | Compound No. | Coupler | Yield (%) (appearance) |
|---|---|---|---|
| 31 | 45 | 3-hydroxy-N-(4-chloro-2-methylphenyl)-2-naphthamide | 80.0 (red) |
| 32 | 77 | 3-hydroxy-2-naphthoic acid benzylidenehydrazide | 92.0 (red) |
| 33 | 58 | N-phenyl-3-hydroxy-benzo[a]carbazole-2-carboxamide | 82.0 (dark red) |
| 34 | 90 | 3-hydroxy-benzo[a]carbazole-2-carboxylic acid benzylidenehydrazide | 65.1 (dark red) |
| 35 | 84 | 3-hydroxy-2-naphthoic acid (2-chlorobenzylidene)hydrazide | 85.0 (red) |

TABLE-1-continued

| Example No. | Compound No. | Coupler | Yield (%) (appearance) |
|---|---|---|---|
| 40 | 164 | 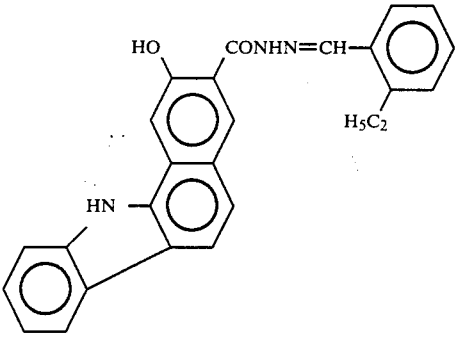 | 71.1 (dark red) |

And, the data such as melting points, elementary analysis values and infrared absorption spectrums of the thus obtained disazo compounds were shown in the following Table-2.

TABLE 2

| Example No. | Compound No. | Melting Point | Element | Calculated value (%) | Measured Value (%) | IR Absorption Spectrum (KBr disc) $\nu_c = 0$ (cm$^{-1}$) |
|---|---|---|---|---|---|---|
| 2 | 1 | 300° C. or more | C | 72.86 | 72.61 | 1675 |
|   |   |   | H | 3.91 | 3.88 |   |
|   |   |   | N | 10.84 | 10.77 |   |
| 3 | 2 | 300° C. or more | C | 73.30 | 73.12 | 1675 |
|   |   |   | H | 4.28 | 4.27 |   |
|   |   |   | N | 10.46 | 10.44 |   |
| 4 | 3 | 300° C. or more | C | 73.30 | 73.04 | 1670 |
|   |   |   | H | 4.28 | 4.30 |   |
|   |   |   | N | 10.46 | 10.46 |   |
| 5 | 4 | 300° C. or more | C | 73.30 | 73.41 | 1665 |
|   |   |   | H | 4.28 | 4.25 |   |
|   |   |   | N | 10.46 | 10.46 |   |
| 6 | 8 | 300° C. or more | C | 70.49 | 70.25 | 1670 |
|   |   |   | H | 4.11 | 4.02 |   |
|   |   |   | N | 10.06 | 9.97 |   |
| 7 | 9 | 300° C. or more | C | 70.49 | 70.21 | 1675 |
|   |   |   | H | 4.11 | 4.07 |   |
|   |   |   | N | 10.06 | 9.97 |   |
| 8 | 10 | 300° C. or more | C | 70.49 | 70.28 | 1670 |
|   |   |   | H | 4.11 | 4.01 |   |
|   |   |   | N | 10.06 | 9.99 |   |
| 9 | 5 | 300° C. or more | C | 73.72 | 73.67 | 1670 |
|   |   |   | H | 4.62 | 4.55 |   |
|   |   |   | N | 9.99 | 10.09 |   |
| 10 | 7 | 300° C. or more | C | 73.72 | 73.58 | 1670 |
|   |   |   | H | 4.62 | 4.53 |   |
|   |   |   | N | 9.99 | 10.10 |   |
| 11 | 11 | 300° C. or more | C | 70.98 | 71.02 | 1665 |
|   |   |   | H | 4.45 | 4.34 |   |
|   |   |   | N | 9.73 | 9.82 |   |
| 12 | 12 | 300° C. or more | C | 70.98 | 70.91 | 1670 |
|   |   |   | H | 4.45 | 4.32 |   |
|   |   |   | N | 9.73 | 9.71 |   |
| 13 | 13 | 300° C. or more | C | 70.98 | 70.74 | 1665 |
|   |   |   | H | 4.45 | 4.33 |   |
|   |   |   | N | 9.73 | 9.60 |   |
| 14 | 14 | 300° C. or more | C | 66.91 | 66.89 | 1675 |
|   |   |   | H | 3.35 | 3.43 |   |
|   |   |   | N | 9.96 | 9.92 |   |
| 15 | 15 | 300° C. or more | C | 66.91 | 66.70 | 1670 |
|   |   |   | H | 3.35 | 3.29 |   |
|   |   |   | N | 9.96 | 9.90 |   |
| 16 | 16 | 300° C. or more | C | 66.91 | 66.83 | 1675 |
|   |   |   | H | 3.35 | 3.42 |   |
|   |   |   | N | 9.96 | 10.08 |   |
| 17 | 17 | 300° C. or more | C | 60.53 | 60.27 | 1675 |
|   |   |   | H | 3.03 | 2.84 |   |
|   |   |   | N | 9.01 | 8.91 |   |
| 18 | 18 | 300° C. or more | C | 60.53 | 60.43 | 1670 |
|   |   |   | H | 3.03 | 2.80 |   |
|   |   |   | N | 9.01 | 8.96 |   | by weight of polycarbonate resin (Panlite-K-1300: produced by TEIJIN K.K.) and 16 parts by weight of tetrahydrofuran by means of a doctor blade. The same was airdried, whereby an about 1 μm-thick charge carrier generating layer was formed.

Then, a solution obtained by mixing and dissolving 2 parts by weight of 9-ethylcarbazole-3-aldehyde-1-methyl-1-phenylhydrazone (charge transfer material), 2 parts by weight of polycarbonate resin (Panlite K-1300: produced by TEIJIN K.K.) and 16 parts by weight of tetrahydrofuran was applied on this charge carrier generating layer by means of a doctor blade, was dried at 80° C. for 2 minutes and in succession was dried at 105° C. for 5 minutes, thereby forming an about 20 μm-thick charge transfer layer. Thus, there was prepared a multilayer type electrophotographic element No. 1 shown in FIG. 3.

EXAMPLE 42 TO EXAMPLE 66

Electrophotographic element No. 2 to No. 26 were prepared by repeating the exactly same procedure as Example 41 except that the disazo compound No. 1 used in Example 41 was replaced by the disazo compound shown in Table-3 referred to afterwards.

EXAMPLE 67 TO EXAMPLE 87

Electrophotographic element No. 27 to No. 47 were prepared by repeating the exactly same procedure as Example 41 except that 1-phenyl-3-(4-diethylaminostyryl)-5-(4-diethylaminophenyl)pyrazolone was used as the charge transfer material and the disazo compounds shown in Table 4 referred to afterwards were used.

EXAMPLE 88 TO EXAMPLE 106

Electrophotographic element No. 48 to No. 66 were prepared by repeating the exactly same procedure as Example 41 except that 9-(4-diethylaminostyryl)anthracene was used as the charge transfer material and the disazo compound shown in Table-5 referred to afterwards.

EXAMPLE 107 TO EXAMPLE 114

Electrophotographic element No. 67 to No. 74 were prepared by repeating the exactly same procedure as Example 41 except that 1,1-bis(4-dibenzylaminophenyl)propane was used as the charge transfer material and the disazo compound shown in Table-6 referred to afterwards was used.

These electrophotographic elements No. 1 to No. 74 were subjected to −6 KV corona discharge for 20 seconds by means of an electrostatic copying paper tester (SP428 Type: produced by Kawaguchi Electro Works) and charged negatively. Thereafter these electrophotographic elements were left standing in the dark for 20 seconds to measure the surface potential Vpo(V) at that time. In succession, said elements were exposed to radiation of light from a tungsten lamp so that the intensity of illumination on their surfaces might be 4.5 lux. and, the time (second) required until the surface potential was reduced to ½ of Vpo was found out and the exposure amount $E_{\frac{1}{2}}$ (lux.sec) was calculated therefrom on each element. The thus obtained results were shown in Table-3–Table-6.

TABLE 3

| Example No. | Electrophotographic Element No. | Disazo Compound No. | Vpo (volt) | $E_{\frac{1}{2}}$ (lux · sec) |
|---|---|---|---|---|
| 41 | 1 | 1 | 1009 | 12.5 |
| 42 | 2 | 2 | 465 | 4.0 |
| 43 | 3 | 8 | 252 | 9.7 |
| 44 | 4 | 14 | 1319 | 2.3 |
| 45 | 5 | 15 | 1260 | 7.9 |
| 46 | 6 | 16 | 852 | 6.2 |
| 47 | 7 | 17 | 1227 | 2.4 |
| 48 | 8 | 18 | 1224 | 4.7 |
| 49 | 9 | 19 | 780 | 8.3 |
| 50 | 10 | 20 | 1211 | 2.7 |
| 51 | 11 | 21 | 1163 | 7.5 |
| 52 | 12 | 22 | 749 | 9.2 |
| 53 | 13 | 23 | 1301 | 3.1 |
| 54 | 14 | 24 | 1215 | 8.5 |
| 55 | 15 | 25 | 830 | 9.0 |
| 56 | 16 | 26 | 1195 | 6.5 |
| 57 | 17 | 27 | 928 | 9.9 |
| 58 | 18 | 29 | 1241 | 8.8 |
| 59 | 19 | 30 | 721 | 12.1 |
| 60 | 20 | 32 | 1270 | 9.9 |
| 61 | 21 | 58 | 738 | 2.0 |
| 62 | 22 | 62 | 922 | 4.8 |
| 63 | 23 | 84 | 1238 | 3.9 |
| 64 | 24 | 85 | 1141 | 8.3 |
| 65 | 25 | 90 | 1140 | 1.3 |
| 66 | 26 | 93 | 1208 | 3.9 |

TABLE 4

| Example No. | Electrophotographic Element No. | Disazo Compound No. | Vpo (volt) | $E_{\frac{1}{2}}$ (lux · sec) |
|---|---|---|---|---|
| 67 | 27 | 1 | 1009 | 12.5 |
| 68 | 28 | 2 | 465 | 4.0 |
| 69 | 29 | 3 | 1082 | 13.2 |
| 70 | 30 | 4 | 916 | 8.2 |
| 71 | 31 | 5 | 948 | 15.2 |
| 72 | 32 | 6 | 237 | 5.7 |
| 73 | 33 | 14 | 1123 | 2.2 |
| 74 | 34 | 15 | 1044 | 9.9 |
| 75 | 35 | 17 | 1227 | 2.4 |
| 76 | 36 | 18 | 1045 | 5.5 |
| 77 | 37 | 20 | 1151 | 3.0 |
| 78 | 31 | 21 | 1022 | 8.5 |
| 79 | 39 | 23 | 1198 | 3.3 |
| 80 | 40 | 24 | 995 | 9.1 |
| 81 | 41 | 26 | 1244 | 7.1 |
| 82 | 42 | 29 | 1176 | 7.8 |
| 83 | 43 | 32 | 1235 | 8.2 |
| 84 | 44 | 58 | 208 | 0.8 |
| 85 | 45 | 84 | 1250 | 4.1 |
| 86 | 46 | 87 | 1100 | 10.5 |
| 87 | 47 | 94 | 1095 | 5.5 |

TABLE 5

| Example No. | Electrophotographic Element No. | Disazo Compound No. | Vpo (volt) | $E_{\frac{1}{2}}$ (lux · sec) |
|---|---|---|---|---|
| 88 | 48 | 2 | 1436 | 13.9 |
| 89 | 49 | 3 | 1145 | 15.0 |
| 90 | 50 | 4 | 1233 | 19.1 |
| 91 | 51 | 7 | 884 | 13.7 |
| 92 | 52 | 14 | 1240 | 2.9 |
| 93 | 53 | 15 | 1258 | 11.8 |
| 94 | 54 | 16 | 1526 | 10.5 |
| 95 | 55 | 17 | 1121 | 2.9 |
| 96 | 56 | 18 | 1164 | 6.1 |
| 97 | 57 | 19 | 1406 | 18.4 |
| 98 | 58 | 20 | 1310 | 3.5 |
| 99 | 59 | 23 | 1227 | 4.3 |
| 100 | 60 | 32 | 1338 | 18.4 |
| 101 | 61 | 33 | 1085 | 10.9 |
| 102 | 62 | 34 | 1246 | 5.7 |
| 103 | 63 | 58 | 940 | 2.3 |
| 104 | 64 | 84 | 1195 | 3.9 | trophotographic elements according to the present invention are high in sensitivity and their sensitive wavelengths cover about 460 to 600 nm.

Further, Electrophotographic Element No. 4 and No. 7 of the present invention were each subjected to 10,000 time-repeated reproduction by means of a copying machine RICOPY-P-500 manufactured by RICOH COMPANY, LTD.

As the result, each electrophotographic element was found to produce a clear-cut image without any change caused by repetition of copying processes. It may be understood therefrom that the electrophotographic elements of the present invention are also superior in durability.

I claim:

1. An electrophotographic element comprising an electrically conductive substrate and a photosensitive layer, formed on said substrate, which is consisted essentially of a disazo compound as a charge carrier generating material represented by the general formula (VIII):

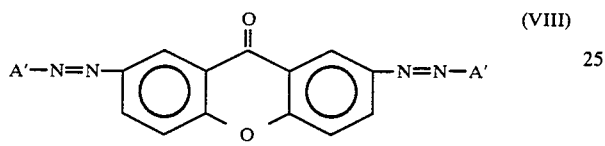

(VIII)

(wherein, A' stands for a coupler group.), a charge transfer material and an insulating binder.

2. An element according to claim 1 wherein A' in the general formula (VIII) is selected from the group of structural formulas represented by the following (IX), (X), (XI), (XII), (XIII), (XIV), (XV), (XVI) and (XVII) [wherein, in the above mentioned formulas, namely

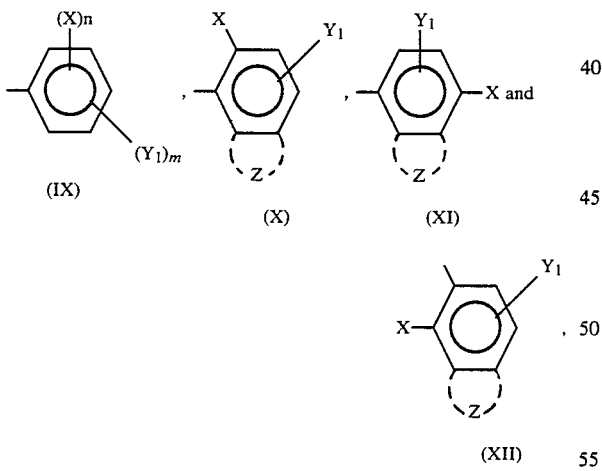

X, $Y_1$, Z, m and n each stands for the following matters:

X:

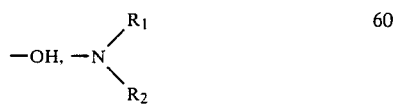

or —NHSO$_2$—R$_3$ (R$_1$ and R$_2$ each stands for hydrogen or a substituted or unsubstituted alkyl group, and R$_3$ stands for a substituted or unsubstituted alkyl group or a substituted or unsubstituted aryl group.)

$Y_1$: hydrogen, halogen, a substituted or unsubstituted alkyl group, a substituted or unsubstituted alkoxy group, a carboxy group, a sulfogroup, a substituted or unsubstituted sulfamoyl group or

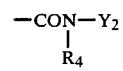

[R$_4$ stands for hydrogen, an alkyl group or its substitution product, and a phenyl group or its substitution product, and Y$_2$ stands for a hydrocarbon ring group or its substitution product or a heterocyclic group or its substitution product or

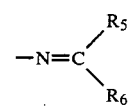

(wherein, R$_5$ stands for a hydrocarbon cyclic group or its substitution product, a heterocyclic group or its substitution product or a styryl group or its substitution product, R$_6$ stands for hydrogen, an alkyl group, a phenyl group or its substitution product, or R$_5$ and R$_6$ may form a ring together with carbon atoms bonded thereto.)]

Z: a hydrocarbon ring or its substitution product or a heterocyclic ring or its substitution product n: an integer of 1 or 2 m: an integer of 1 or 2

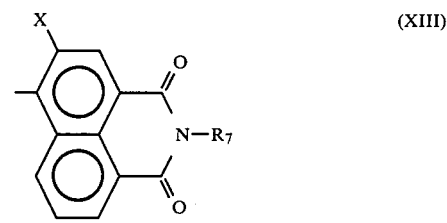

(XIII)

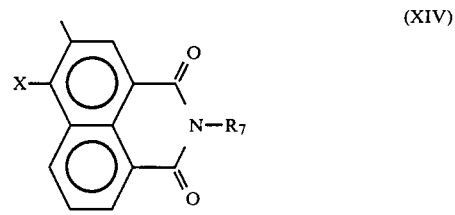

(XIV)

[in the formulas (XIII) and (XIV), R$_7$ stands for a substituted or unsubstituted hydrocarbon group and X is the same as defined above.]

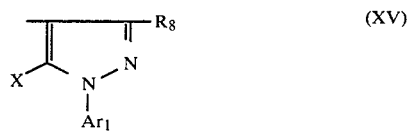

(XV)

[wherein, R$_8$ stands for an alkyl group, a carbamoyl group, a carboxyl group or its ester, Ar$_1$ stands for a hydrocarbon ring group or its substitution product, and X is the same as defined above.]

trophotographic elements according to the present invention are high in sensitivity and their sensitive wavelengths cover about 460 to 600 nm.

Further, Electrophotographic Element No. 4 and No. 7 of the present invention were each subjected to 10,000 time-repeated reproduction by means of a copying machine RICOPY-P-500 manufactured by RICOH COMPANY, LTD.

As the result, each electrophotographic element was found to produce a clear-cut image without any change caused by repetition of copying processes. It may be understood therefrom that the electrophotographic elements of the present invention are also superior in durability.

I claim:

1. An electrophotographic element comprising an electrically conductive substrate and a photosensitive layer, formed on said substrate, which is consisted essentially of a disazo compound as a charge carrier generating material represented by the general formula (VIII):

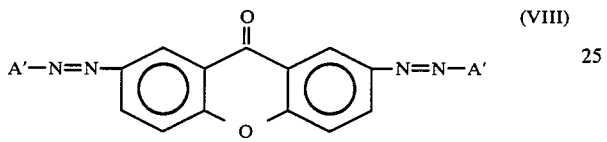

(wherein, A' stands for a coupler group.), a charge transfer material and an insulating binder.

2. An element according to claim 1 wherein A' in the general formula (VIII) is selected from the group of structural formulas represented by the following (IX), (X), (XI), (XII), (XIII), (XIV), (XV), (XVI) and (XVII) [wherein, in the above mentioned formulas, namely

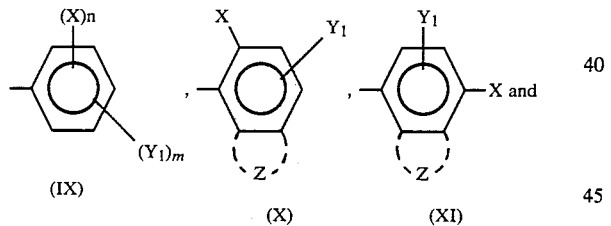

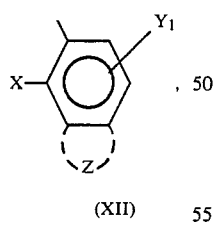

$X$, $Y_1$, $Z$, $m$ and $n$ each stands for the following matters:

X:

or $-NHSO_2-R_3$ ($R_1$ and $R_2$ each stands for hydrogen or a substituted or unsubstituted alkyl group, and $R_3$ stands for a substituted or unsubstituted alkyl group or a substituted or unsubstituted aryl group.)

$Y_1$: hydrogen, halogen, a substituted or unsubstituted alkyl group, a substituted or unsubstituted alkoxy group, a carboxy group, a sulfogroup, a substituted or unsubstituted sulfamoyl group or

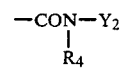

[$R_4$ stands for hydrogen, an alkyl group or its substitution product, and a phenyl group or its substitution product, and $Y_2$ stands for a hydrocarbon ring group or its substitution product or a heterocyclic group or its substitution product or

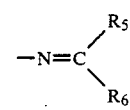

(wherein, $R_5$ stands for a hydrocarbon cyclic group or its substitution product, a heterocyclic group or its substitution product or a styryl group or its substitution product, $R_6$ stands for hydrogen, an alkyl group, a phenyl group or its substitution product, or $R_5$ and $R_6$ may form a ring together with carbon atoms bonded thereto.)]

Z: a hydrocarbon ring or its substitution product or a heterocyclic ring or its substitution product n: an integer of 1 or 2 m: an integer of 1 or 2

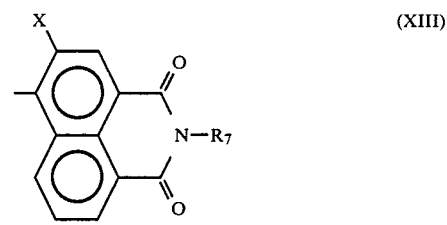

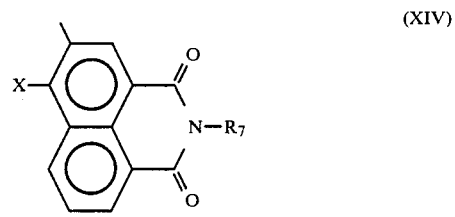

[in the formulas (XIII) and (XIV), $R_7$ stands for a substituted or unsubstituted hydrocarbon group and X is the same as defined above.]

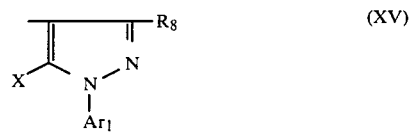

[wherein, $R_8$ stands for an alkyl group, a carbamoyl group, a carboxyl group or its ester, $Ar_1$ stands for a hydrocarbon ring group or its substitution product, and X is the same as defined above.]

TABLE-1-continued

| Example No. | Compound No. | Coupler | Yield (%) (appearance) |
|---|---|---|---|
| 40 | 164 | 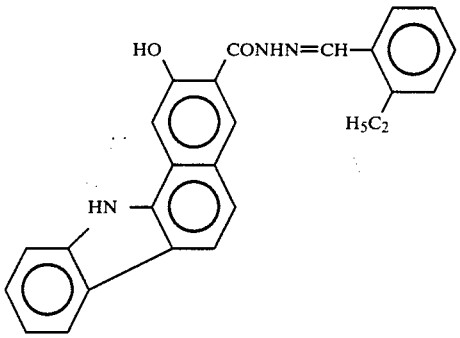 | 71.1 (dark red) |

And, the data such as melting points, elementary analysis values and infrared absorption spectrums of the thus obtained disazo compounds were shown in the following Table-2.

TABLE 2

| Example No. | Compound No. | Melting Point | Element | Elementary Analysis Value Calculated value (%) | Measured Value (%) | IR Absorption Spectrum (KBr disc) $\nu_c = 0$ (cm$^{-1}$) |
|---|---|---|---|---|---|---|
| 2 | 1 | 300° C. or more | C | 72.86 | 72.61 | 1675 |
|   |   |   | H | 3.91 | 3.88 |   |
|   |   |   | N | 10.84 | 10.77 |   |
| 3 | 2 | 300° C. or more | C | 73.30 | 73.12 | 1675 |
|   |   |   | H | 4.28 | 4.27 |   |
|   |   |   | N | 10.46 | 10.44 |   |
| 4 | 3 | 300° C. or more | C | 73.30 | 73.04 | 1670 |
|   |   |   | H | 4.28 | 4.30 |   |
|   |   |   | N | 10.46 | 10.46 |   |
| 5 | 4 | 300° C. or more | C | 73.30 | 73.41 | 1665 |
|   |   |   | H | 4.28 | 4.25 |   |
|   |   |   | N | 10.46 | 10.46 |   |
| 6 | 8 | 300° C. or more | C | 70.49 | 70.25 | 1670 |
|   |   |   | H | 4.11 | 4.02 |   |
|   |   |   | N | 10.06 | 9.97 |   |
| 7 | 9 | 300° C. or more | C | 70.49 | 70.21 | 1675 |
|   |   |   | H | 4.11 | 4.07 |   |
|   |   |   | N | 10.06 | 9.97 |   |
| 8 | 10 | 300° C. or more | C | 70.49 | 70.28 | 1670 |
|   |   |   | H | 4.11 | 4.01 |   |
|   |   |   | N | 10.06 | 9.99 |   |
| 9 | 5 | 300° C. or more | C | 73.72 | 73.67 | 1670 |
|   |   |   | H | 4.62 | 4.55 |   |
|   |   |   | N | 9.99 | 10.09 |   |
| 10 | 7 | 300° C. or more | C | 73.72 | 73.58 | 1670 |
|   |   |   | H | 4.62 | 4.53 |   |
|   |   |   | N | 9.99 | 10.10 |   |
| 11 | 11 | 300° C. or more | C | 70.98 | 71.02 | 1665 |
|   |   |   | H | 4.45 | 4.34 |   |
|   |   |   | N | 9.73 | 9.82 |   |
| 12 | 12 | 300° C. or more | C | 70.98 | 70.91 | 1670 |
|   |   |   | H | 4.45 | 4.32 |   |
|   |   |   | N | 9.73 | 9.71 |   |
| 13 | 13 | 300° C. or more | C | 70.98 | 70.74 | 1665 |
|   |   |   | H | 4.45 | 4.33 |   |
|   |   |   | N | 9.73 | 9.60 |   |
| 14 | 14 | 300° C. or more | C | 66.91 | 66.89 | 1675 |
|   |   |   | H | 3.35 | 3.43 |   |
|   |   |   | N | 9.96 | 9.92 |   |
| 15 | 15 | 300° C. or more | C | 66.91 | 66.70 | 1670 |
|   |   |   | H | 3.35 | 3.29 |   |
|   |   |   | N | 9.96 | 9.90 |   |
| 16 | 16 | 300° C. or more | C | 66.91 | 66.83 | 1675 |
|   |   |   | H | 3.35 | 3.42 |   |
|   |   |   | N | 9.96 | 10.08 |   |
| 17 | 17 | 300° C. or more | C | 60.53 | 60.27 | 1675 |
|   |   |   | H | 3.03 | 2.84 |   |
|   |   |   | N | 9.01 | 8.91 |   |
| 18 | 18 | 300° C. or more | C | 60.53 | 60.43 | 1670 |
|   |   |   | H | 3.03 | 2.80 |   |
|   |   |   | N | 9.01 | 8.96 |   | by weight of polycarbonate resin (Panlite-K-1300: produced by TEIJIN K.K.) and 16 parts by weight of tetrahydrofuran by means of a doctor blade. The same was airdried, whereby an about 1 μm-thick charge carrier generating layer was formed.

Then, a solution obtained by mixing and dissolving 2 parts by weight of 9-ethylcarbazole-3-aldehyde-1-methyl-1-phenylhydrazone (charge transfer material), 2 parts by weight of polycarbonate resin (Panlite K-1300: produced by TEIJIN K.K.) and 16 parts by weight of tetrahydrofuran was applied on this charge carrier generating layer by means of a doctor blade, was dried at 80° C. for 2 minutes and in succession was dried at 105° C. for 5 minutes, thereby forming an about 20 μm-thick charge transfer layer. Thus, there was prepared a multilayer type electrophotographic element No. 1 shown in FIG. 3.

EXAMPLE 42 TO EXAMPLE 66

Electrophotographic element No. 2 to No. 26 were prepared by repeating the exactly same procedure as Example 41 except that the disazo compound No. 1 used in Example 41 was replaced by the disazo compound shown in Table-3 referred to afterwards.

EXAMPLE 67 TO EXAMPLE 87

Electrophotographic element No. 27 to No. 47 were prepared by repeating the exactly same procedure as Example 41 except that 1-phenyl-3-(4-diethylaminostyryl)-5-(4-diethylaminophenyl)pyrazolone was used as the charge transfer material and the disazo compounds shown in Table 4 referred to afterwards were used.

EXAMPLE 88 TO EXAMPLE 106

Electrophotographic element No. 48 to No. 66 were prepared by repeating the exactly same procedure as Example 41 except that 9-(4-diethylaminostyryl)anthracene was used as the charge transfer material and the disazo compound shown in Table-5 referred to afterwards.

EXAMPLE 107 TO EXAMPLE 114

Electrophotographic element No. 67 to No. 74 were prepared by repeating the exactly same procedure as Example 41 except that 1,1-bis(4-dibenzylaminophenyl)propane was used as the charge transfer material and the disazo compound shown in Table-6 referred to afterwards was used.

These electrophotographic elements No. 1 to No. 74 were subjected to −6 KV corona discharge for 20 seconds by means of an electrostatic copying paper tester (SP428 Type: produced by Kawaguchi Electro Works) and charged negatively. Thereafter these electrophotographic elements were left standing in the dark for 20 seconds to measure the surface potential Vpo(V) at that time. In succession, said elements were exposed to radiation of light from a tungsten lamp so that the intensity of illumination on their surfaces might be 4.5 lux. and, the time (second) required until the surface potential was reduced to ½ of Vpo was found out and the exposure amount $E_{\frac{1}{2}}$ (lux.sec) was calculated therefrom on each element. The thus obtained results were shown in Table-3–Table-6.

TABLE 3

| Example No. | Electrophotographic Element No. | Disazo Compound No. | Vpo (volt) | $E_{\frac{1}{2}}$ (lux · sec) |
|---|---|---|---|---|
| 41 | 1 | 1 | 1009 | 12.5 |
| 42 | 2 | 2 | 465 | 4.0 |
| 43 | 3 | 8 | 252 | 9.7 |
| 44 | 4 | 14 | 1319 | 2.3 |
| 45 | 5 | 15 | 1260 | 7.9 |
| 46 | 6 | 16 | 852 | 6.2 |
| 47 | 7 | 17 | 1227 | 2.4 |
| 48 | 8 | 18 | 1224 | 4.7 |
| 49 | 9 | 19 | 780 | 8.3 |
| 50 | 10 | 20 | 1211 | 2.7 |
| 51 | 11 | 21 | 1163 | 7.5 |
| 52 | 12 | 22 | 749 | 9.2 |
| 53 | 13 | 23 | 1301 | 3.1 |
| 54 | 14 | 24 | 1215 | 8.5 |
| 55 | 15 | 25 | 830 | 9.0 |
| 56 | 16 | 26 | 1195 | 6.5 |
| 57 | 17 | 27 | 928 | 9.9 |
| 58 | 18 | 29 | 1241 | 8.8 |
| 59 | 19 | 30 | 721 | 12.1 |
| 60 | 20 | 32 | 1270 | 9.9 |
| 61 | 21 | 58 | 738 | 2.0 |
| 62 | 22 | 62 | 922 | 4.8 |
| 63 | 23 | 84 | 1238 | 3.9 |
| 64 | 24 | 85 | 1141 | 8.3 |
| 65 | 25 | 90 | 1140 | 1.3 |
| 66 | 26 | 93 | 1208 | 3.9 |

TABLE 4

| Example No. | Electrophotographic Element No. | Disazo Compound No. | Vpo (volt) | $E_{\frac{1}{2}}$ (lux · sec) |
|---|---|---|---|---|
| 67 | 27 | 1 | 1009 | 12.5 |
| 68 | 28 | 2 | 465 | 4.0 |
| 69 | 29 | 3 | 1082 | 13.2 |
| 70 | 30 | 4 | 916 | 8.2 |
| 71 | 31 | 5 | 948 | 15.2 |
| 72 | 32 | 6 | 237 | 5.7 |
| 73 | 33 | 14 | 1123 | 2.2 |
| 74 | 34 | 15 | 1044 | 9.9 |
| 75 | 35 | 17 | 1227 | 2.4 |
| 76 | 36 | 18 | 1045 | 5.5 |
| 77 | 37 | 20 | 1151 | 3.0 |
| 78 | 31 | 21 | 1022 | 8.5 |
| 79 | 39 | 23 | 1198 | 3.3 |
| 80 | 40 | 24 | 995 | 9.1 |
| 81 | 41 | 26 | 1244 | 7.1 |
| 82 | 42 | 29 | 1176 | 7.8 |
| 83 | 43 | 32 | 1235 | 8.2 |
| 84 | 44 | 58 | 208 | 0.8 |
| 85 | 45 | 84 | 1250 | 4.1 |
| 86 | 46 | 87 | 1100 | 10.5 |
| 87 | 47 | 94 | 1095 | 5.5 |

TABLE 5

| Example No. | Electrophotographic Element No. | Disazo Compound No. | Vpo (volt) | $E_{\frac{1}{2}}$ (lux · sec) |
|---|---|---|---|---|
| 88 | 48 | 2 | 1436 | 13.9 |
| 89 | 49 | 3 | 1145 | 15.0 |
| 90 | 50 | 4 | 1233 | 19.1 |
| 91 | 51 | 7 | 884 | 13.7 |
| 92 | 52 | 14 | 1240 | 2.9 |
| 93 | 53 | 15 | 1258 | 11.8 |
| 94 | 54 | 16 | 1526 | 10.5 |
| 95 | 55 | 17 | 1121 | 2.9 |
| 96 | 56 | 18 | 1164 | 6.1 |
| 97 | 57 | 19 | 1406 | 18.4 |
| 98 | 58 | 20 | 1310 | 3.5 |
| 99 | 59 | 23 | 1227 | 4.3 |
| 100 | 60 | 32 | 1338 | 18.4 |
| 101 | 61 | 33 | 1085 | 10.9 |
| 102 | 62 | 34 | 1246 | 5.7 |
| 103 | 63 | 58 | 940 | 2.3 |
| 104 | 64 | 84 | 1195 | 3.9 |

TABLE-1-continued
| Example No. | Compound No. | Coupler | Yield (%) (appearance) |
|---|---|---|---|
| 31 | 45 | 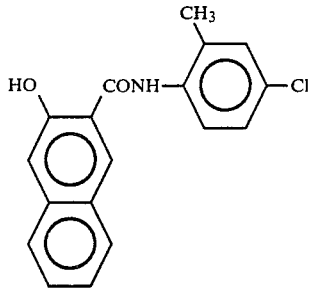 | 80.0 (red) |
| 32 | 77 | 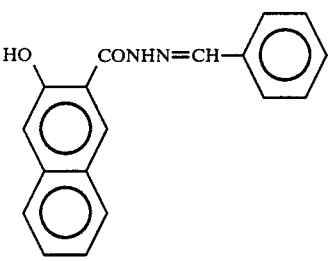 | 92.0 (red) |
| 33 | 58 | 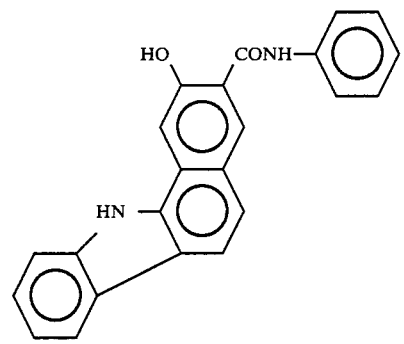 | 82.0 (dark red) |
| 34 | 90 | 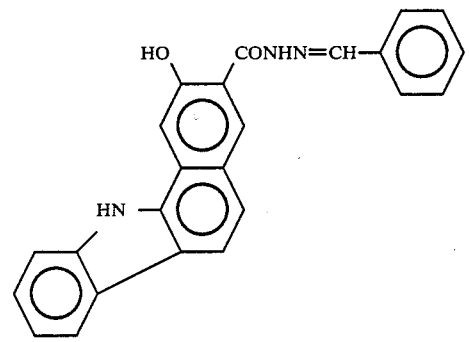 | 65.1 (dark red) |
| 35 | 84 | 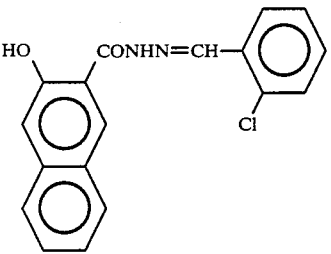 | 85.0 (red) |

UNITED STATES PATENT AND TRADEMARK OFFICE
CERTIFICATE OF CORRECTION

PATENT NO. : 4,540,643

DATED : September 10, 1985

INVENTOR(S) : Kyoji TSUTSUI

It is certified that error appears in the above-identified patent and that said Letters Patent is hereby corrected as shown below:

Column 80, line 31; change "claim 6" to ---claim 1---.

Signed and Sealed this

Seventeenth Day of June 1986

[SEAL]

Attest:

DONALD J. QUIGG

Attesting Officer

Commissioner of Patents and Trademarks